(12) United States Patent
Faries, Jr. et al.

(10) Patent No.: US 8,920,387 B2
(45) Date of Patent: Dec. 30, 2014

(54) METHOD AND APPARATUS FOR PRESSURE INFUSION AND TEMPERATURE CONTROL OF INFUSED LIQUIDS

(75) Inventors: Durward I. Faries, Jr., McLean, VA (US); Bruce Heymann, Vienna, VA (US); Calvin Blankenship, Centreville, VA (US); George T. DuBose, Jr., High View, WV (US)

(73) Assignee: Medical Solutions, Inc., Chantilly, VA (US)

( * ) Notice: Subject to any disclaimer, the term of this patent is extended or adjusted under 35 U.S.C. 154(b) by 642 days.

(21) Appl. No.: 12/040,933

(22) Filed: Mar. 3, 2008
(Under 37 CFR 1.47)

(65) Prior Publication Data

US 2008/0147016 A1 Jun. 19, 2008

Related U.S. Application Data

(60) Division of application No. 10/913,512, filed on Aug. 9, 2004, now Pat. No. 7,942,851, which is a continuation of application No. 09/380,507, filed as application No. PCT/US98/04199 on Mar. 3, 1998, now Pat. No. 6,824,528.

(60) Provisional application No. 60/040,885, filed on Mar. 3, 1997, provisional application No. 60/062,315, filed on Oct. 17, 1997.

(51) Int. Cl.
*A61B 17/70* (2006.01)
*A61M 5/148* (2006.01)
*A61M 5/44* (2006.01)
*A61M 5/142* (2006.01)
*A61M 5/168* (2006.01)
*A61M 5/172* (2006.01)

(52) U.S. Cl.
CPC .............. *A61M 5/148* (2013.01); *A61M 5/1483* (2013.01); *A61M 5/44* (2013.01); *A61M 5/445* (2013.01); *A61M 5/1424* (2013.01); *A61M 5/1689* (2013.01); *A61M 5/172* (2013.01); *A61M 2205/3368* (2013.01); *A61M 2205/3653* (2013.01); *A61M 2209/04* (2013.01)
USPC .................................................. 604/253

(58) Field of Classification Search
USPC ............................... 604/65–67, 113, 251–255
See application file for complete search history.

(56) References Cited

U.S. PATENT DOCUMENTS 522,866 A 7/1894 Weinhagen et al.
558,979 A 4/1896 Noble
(Continued)

FOREIGN PATENT DOCUMENTS

DE 3709122 9/1988
DE 3742927 7/1989
(Continued)

OTHER PUBLICATIONS

*Health Devices*, vol. 25, No. 10, Oct. 1996.
(Continued)

*Primary Examiner* — Aarti B Berdichevsky
*Assistant Examiner* — Bradley Osinski
(74) *Attorney, Agent, or Firm* — Edell, Shapiro & Finnan, LLC

(57) ABSTRACT

A method and apparatus for pressure infusion and temperature control of infused liquids including an infrared sensing device mounted proximate a drip chamber to ascertain drip count. The infrared sensing device having particular features such as emission and detection window shapes, arrangement of emission and detection windows and different numbers of emitters and detectors.

16 Claims, 15 Drawing Sheets

(56) References Cited

U.S. PATENT DOCUMENTS

| | | |
|---|---|---|
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,493,450 A | 5/1924 | Richardson |
| 1,659,719 A | 2/1928 | Blake |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,175,099 A | 10/1939 | Abbott |
| 2,204,764 A | 6/1940 | Mayo |
| 2,214,215 A | 9/1940 | Watermann et al. |
| 2,254,994 A | 9/1941 | Butland |
| 2,470,481 A | 5/1949 | Freeman |
| 2,576,874 A | 11/1951 | Acton |
| 2,701,789 A | 2/1955 | White |
| 2,713,112 A | 7/1955 | Mills et al. |
| 2,741,099 A | 4/1956 | Beane |
| 2,766,907 A | 10/1956 | Wallace, Jr. |
| 2,841,132 A | 7/1958 | Philipp |
| 2,880,764 A | 4/1959 | Pelavin |
| 2,885,526 A | 5/1959 | Paulding |
| 2,910,981 A | 11/1959 | Wilson et al. |
| 2,990,875 A | 7/1961 | Samuels et al. |
| 2,994,760 A | 8/1961 | Pecoraro et al. |
| 3,051,582 A | 8/1962 | Muckler et al. |
| 3,140,716 A | 7/1964 | Harrison et al. |
| 3,157,727 A | 11/1964 | Hardy et al. |
| 3,193,339 A | 7/1965 | Cooper |
| 3,241,603 A | 3/1966 | Nagata |
| 3,247,851 A | 4/1966 | Seibert |
| 3,255,812 A | 6/1966 | Bayane et al. |
| 3,293,868 A | 12/1966 | Gonzalez |
| 3,329,202 A | 7/1967 | Birman |
| 3,353,589 A | 11/1967 | Tope et al. |
| 3,370,153 A | 2/1968 | Du Fresne et al. |
| 3,386,498 A | 6/1968 | Funfstuck |
| 3,475,590 A | 10/1969 | Pins |
| 3,485,245 A | 12/1969 | Lahr et al. |
| 3,500,366 A | 3/1970 | Chesney et al. |
| 3,526,134 A | 9/1970 | Schaus |
| 3,536,132 A | 10/1970 | Pecoraro et al. |
| 3,551,641 A | 12/1970 | Truhan |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,059 A | 10/1971 | Ersek |
| 3,612,165 A | 10/1971 | Haynes |
| 3,614,385 A | 10/1971 | Horstmann |
| 3,629,552 A | 12/1971 | Edging |
| 3,636,767 A | 1/1972 | Duffy |
| 3,640,277 A | 2/1972 | Adelberg |
| 3,651,695 A | 3/1972 | Brown |
| 3,713,302 A | 1/1973 | Reviel |
| 3,777,187 A | 12/1973 | Kohn |
| 3,801,278 A | 4/1974 | Wagner et al. |
| 3,826,305 A | 7/1974 | Fishman |
| 3,845,661 A | 11/1974 | Hollweck et al. |
| 3,858,106 A | 12/1974 | Launius |
| 3,879,171 A | 4/1975 | Tulis |
| 3,895,741 A | 7/1975 | Nugent |
| 3,908,652 A | 9/1975 | Weissinger |
| 3,940,742 A | 2/1976 | Hudspeth et al. |
| 4,009,615 A | 3/1977 | Ruhl |
| 4,024,377 A | 5/1977 | Henke |
| 4,038,519 A | 7/1977 | Foucras |
| 4,063,551 A * | 12/1977 | Sweeney ............... 600/479 |
| 4,084,080 A | 4/1978 | McMahan |
| 4,090,514 A | 5/1978 | Hinck et al. |
| 4,098,123 A | 7/1978 | Granzow, Jr. |
| 4,121,574 A | 10/1978 | Lester |
| 4,138,890 A | 2/1979 | Brown |
| 4,167,663 A | 9/1979 | Granzow, Jr. et al. |
| 4,187,847 A | 2/1980 | Loeser |
| 4,189,995 A | 2/1980 | Löhr et al. |
| 4,233,495 A | 11/1980 | Scoville et al. |
| 4,293,762 A | 10/1981 | Ogawa |
| 4,309,592 A | 1/1982 | Le Boeuf |
| 4,314,484 A | 2/1982 | Bowman |
| 4,318,276 A | 3/1982 | Sato et al. |
| 4,328,676 A | 5/1982 | Reed |
| 4,329,569 A | 5/1982 | Hjortsberg et al. |
| 4,331,859 A | 5/1982 | Thomas et al. |
| 4,336,435 A | 6/1982 | Kashyap et al. |
| 4,356,383 A | 10/1982 | Dahlberg |
| 4,364,234 A | 12/1982 | Reed |
| 4,375,813 A | 3/1983 | Hessel |
| 4,384,578 A | 5/1983 | Winkler |
| 4,397,648 A | 8/1983 | Knute |
| 4,407,133 A | 10/1983 | Edmonson |
| 4,419,568 A | 12/1983 | Van Overloop |
| 4,430,077 A | 2/1984 | Mittleman et al. |
| 4,430,078 A | 2/1984 | Sprague |
| 4,432,761 A | 2/1984 | Dawe |
| 4,455,478 A | 6/1984 | Guibert |
| 4,464,563 A | 8/1984 | Jewett |
| 4,476,877 A | 10/1984 | Barker |
| 4,481,410 A | 11/1984 | Bortnick |
| 4,490,884 A | 1/1985 | Vickers |
| 4,495,402 A | 1/1985 | Burdick et al. |
| 4,498,901 A | 2/1985 | Finch |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,531,941 A | 7/1985 | Zasuwa |
| 4,532,414 A | 7/1985 | Shah et al. |
| 4,533,350 A * | 8/1985 | Danby et al. ................ 604/253 |
| 4,543,095 A | 9/1985 | Jensen |
| 4,551,136 A | 11/1985 | Mandl |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,613,327 A | 9/1986 | Tegrarian |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,673,820 A * | 6/1987 | Kamen ............... 250/573 |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,682,979 A | 7/1987 | Girouard |
| 4,684,367 A | 8/1987 | Schaffer et al. |
| 4,705,505 A | 11/1987 | Fried |
| 4,707,587 A | 11/1987 | Greenblatt |
| 4,709,135 A | 11/1987 | Dietrich et al. |
| 4,718,896 A | 1/1988 | Arndt et al. |
| 4,726,193 A | 2/1988 | Burke et al. |
| 4,735,609 A | 4/1988 | Comeau et al. |
| 4,745,248 A | 5/1988 | Hayes |
| 4,747,450 A | 5/1988 | Ikegame et al. |

(56) References Cited

U.S. PATENT DOCUMENTS

| | | |
|---|---|---|
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,554 A | 4/1989 | Trachtenberg et al. |
| 4,823,833 A | 4/1989 | Hogan et al. |
| 4,832,689 A | 5/1989 | Mauerer et al. |
| 4,844,074 A | 7/1989 | Kurucz |
| 4,844,397 A | 7/1989 | Skakoon et al. |
| 4,847,470 A | 7/1989 | Bakke |
| 4,859,360 A | 8/1989 | Suzuki et al. |
| 4,874,033 A | 10/1989 | Nicholas Marchiani Chatelain et al. |
| 4,874,359 A | 10/1989 | White et al. |
| 4,878,537 A | 11/1989 | Verkaart |
| 4,883,117 A | 11/1989 | Dobbs et al. |
| 4,894,207 A | 1/1990 | Archer et al. |
| 4,900,308 A | 2/1990 | Verkaart |
| 4,904,848 A | 2/1990 | Colevas |
| 4,906,816 A | 3/1990 | van Leerdam |
| 4,910,386 A | 3/1990 | Johnson |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,013,889 A | 5/1991 | Bakke |
| 5,019,047 A | 5/1991 | Kriesel |
| 5,040,380 A | 8/1991 | Gregory |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knoopf et al. |
| 5,063,994 A | 11/1991 | Verkaart |
| 5,073,167 A | 12/1991 | Carr et al. |
| 5,074,658 A | 12/1991 | Tavlarides et al. |
| 5,075,167 A | 12/1991 | Yamauchi et al. |
| 5,081,697 A | 1/1992 | Manella |
| 5,096,078 A | 3/1992 | McQueeny |
| 5,096,822 A | 3/1992 | Rosenkrans, Jr. et al. |
| 5,097,898 A | 3/1992 | Verkaart |
| 5,103,817 A | 4/1992 | Reisdorf et al. |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,153,827 A | 10/1992 | Coutré et al. |
| 5,169,389 A | 12/1992 | Kriesel |
| 5,180,896 A | 1/1993 | Gibby et al. |
| 5,183,994 A | 2/1993 | Bowles, Sr. et al. |
| 5,184,613 A | 2/1993 | Mintz |
| 5,186,057 A * | 2/1993 | Everhart .................... 73/861.41 |
| 5,195,976 A | 3/1993 | Swenson |
| 5,205,820 A | 4/1993 | Kriesel |
| 5,211,631 A | 5/1993 | Sheaff |
| 5,217,064 A | 6/1993 | Kellow et al. |
| 5,232,439 A | 8/1993 | Campbell et al. |
| 5,241,951 A | 9/1993 | Mason et al. |
| 5,243,172 A | 9/1993 | Hazan et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,269,749 A | 12/1993 | Koturov |
| 1,479,451 A | 1/1994 | Buckstein |
| 5,276,310 A | 1/1994 | Schmidt et al. |
| 5,279,558 A | 1/1994 | Kriesel |
| 5,279,598 A | 1/1994 | Sheaff |
| 5,282,264 A | 1/1994 | Reeves et al. |
| 5,290,222 A | 3/1994 | Feng et al. |
| 5,290,230 A | 3/1994 | Ainsworth et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,318,540 A | 6/1994 | Athayde et al. |
| 5,330,431 A | 7/1994 | Herskowitz |
| 5,333,326 A | 8/1994 | Faries, Jr. et al. |
| 5,338,157 A | 8/1994 | Blomquist |
| 5,342,313 A | 8/1994 | Campbell et al. |
| 5,345,923 A | 9/1994 | Luebke et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,417,274 A | 5/1995 | Verkaart |
| 5,420,962 A | 5/1995 | Bakke |
| 5,423,759 A | 6/1995 | Campbell |
| 5,424,512 A | 6/1995 | Turetta et al. |
| 5,433,704 A | 7/1995 | Ross et al. |
| 5,451,209 A | 9/1995 | Ainsworth et al. |
| 5,474,538 A | 12/1995 | Stihler et al. |
| 5,483,799 A | 1/1996 | Dalto |
| 5,485,408 A | 1/1996 | Blomquist |
| 5,492,534 A | 2/1996 | Athayde et al. |
| 5,494,196 A | 2/1996 | Tyner |
| 5,512,043 A | 4/1996 | Verkaart |
| 5,514,095 A | 5/1996 | Brightbill et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,584,811 A | 12/1996 | Ross et al. |
| 5,590,648 A | 1/1997 | Mitchell |
| 5,609,784 A | 3/1997 | Davenport |
| RE35,501 E | 5/1997 | Ross et al. |
| 5,647,854 A | 7/1997 | Olsen et al. |
| 5,649,910 A | 7/1997 | Kriesel et al. |
| 5,653,905 A | 8/1997 | McKinney |
| 5,658,250 A | 8/1997 | Blomquist et al. |
| 5,658,252 A | 8/1997 | Johnson |
| 5,658,478 A | 8/1997 | Roeschel et al. |
| 5,661,978 A | 9/1997 | Holmes et al. |
| 5,662,611 A | 9/1997 | Beiser et al. |
| 5,669,877 A | 9/1997 | Blomquist |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |
| 5,707,151 A | 1/1998 | Parker et al. |
| 5,707,431 A | 1/1998 | Verkaart et al. |
| 5,713,864 A | 2/1998 | Verkaart |
| 5,720,728 A | 2/1998 | Ford |
| 5,729,653 A | 3/1998 | Magliochetti et al. |
| 5,733,263 A | 3/1998 | Wheatman |
| 5,743,878 A | 4/1998 | Ross et al. |
| 5,744,806 A * | 4/1998 | Frojd .................... 250/370.09 |

(56) References Cited

U.S. PATENT DOCUMENTS

| | | |
|---|---|---|
| 5,755,275 A | 5/1998 | Rose et al. |
| 5,772,409 A | 6/1998 | Johnson |
| 5,786,568 A | 7/1998 | McKinney |
| 5,788,669 A | 8/1998 | Peterson |
| 5,788,671 A | 8/1998 | Johnson |
| 5,805,455 A | 9/1998 | Lipps |
| 5,806,528 A | 9/1998 | Magliochetti |
| 5,807,332 A | 9/1998 | Augustine et al. |
| 5,810,771 A | 9/1998 | Blomquist |
| 5,816,797 A | 10/1998 | Shoenfeld |
| 5,823,746 A | 10/1998 | Johnson |
| 5,824,000 A | 10/1998 | Pavlo et al. |
| 5,829,880 A | 11/1998 | Diedrich |
| 5,840,068 A | 11/1998 | Cartledge |
| 5,862,672 A | 1/1999 | Faries, Jr. et al. |
| 5,875,282 A | 2/1999 | Jordan et al. |
| 5,876,370 A | 3/1999 | Blomquist |
| 5,879,143 A | 3/1999 | Cote et al. |
| 5,879,329 A | 3/1999 | Ginsburg |
| 5,891,096 A | 4/1999 | Hyun et al. |
| 5,893,843 A | 4/1999 | Rodrigues |
| 5,910,210 A | 6/1999 | Violi et al. |
| 5,919,218 A | 7/1999 | Carr |
| 5,924,289 A | 7/1999 | Bishop, II |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,700 A | 9/1999 | Kovelman |
| 5,961,492 A | 10/1999 | Kriesel et al. |
| 5,961,700 A | 10/1999 | Oliver |
| 5,961,866 A | 10/1999 | Hansen |
| 5,977,520 A | 11/1999 | Madson, Jr. et al. |
| 5,986,239 A | 11/1999 | Corrigan, III |
| 5,989,238 A | 11/1999 | Ginsburg |
| 6,024,539 A | 2/2000 | Blomquist |
| 6,035,102 A | 3/2000 | Bakke |
| 6,039,926 A | 3/2000 | Goldman |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,124,572 A | 9/2000 | Spilger et al. |
| 6,129,702 A | 10/2000 | Woias et al. |
| 6,139,528 A | 10/2000 | Kistner et al. |
| 6,142,974 A | 11/2000 | Kistner et al. |
| 6,146,359 A | 11/2000 | Carr et al. |
| 6,158,458 A | 12/2000 | Ryan |
| 6,174,300 B1 | 1/2001 | Kriesel et al. |
| 6,175,099 B1 | 1/2001 | Shei et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,236,809 B1 | 5/2001 | Cassidy et al. |
| 6,248,077 B1 | 6/2001 | Elson et al. |
| 6,254,572 B1 | 7/2001 | Knipfer et al. |
| 6,259,067 B1 | 7/2001 | Faries, Jr. et al. |
| 6,261,261 B1 | 7/2001 | Gordon |
| 6,294,762 B1 | 9/2001 | Faries, Jr. et al. |
| 6,315,767 B1 | 11/2001 | Dumont et al. |
| 6,316,750 B1 | 11/2001 | Levin |
| 6,334,707 B1 | 1/2002 | Ku |
| 6,371,121 B1 | 4/2002 | Faries, Jr. et al. |
| 6,376,805 B2 | 4/2002 | Faries, Jr. et al. |
| 6,384,380 B1 | 5/2002 | Faries, Jr. et al. |
| 6,464,666 B1 | 10/2002 | Augustine |
| 6,467,953 B1 | 10/2002 | Faries, Jr. et al. |
| 6,480,257 B2 | 11/2002 | Cassidy et al. |
| 6,524,239 B1 | 2/2003 | Reed et al. |
| 6,553,336 B1 | 4/2003 | Johnson |
| 6,566,631 B2 | 5/2003 | Faries, Jr. et al. |
| 6,607,027 B2 | 8/2003 | Bosch et al. |
| 6,641,556 B1 | 11/2003 | Shigezawa |
| 6,641,602 B2 | 11/2003 | Balding |
| 6,649,040 B1 | 11/2003 | Mirchi et al. |
| 6,660,974 B2 | 12/2003 | Faries, Jr. et al. |
| 6,722,782 B2 | 4/2004 | Faries, Jr. et al. |
| 6,736,788 B1 | 5/2004 | Mongomery |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,788,885 B2 | 9/2004 | Mitsunaga et al. |
| 6,788,997 B1 | 9/2004 | Frederick |
| 6,824,528 B1 | 11/2004 | Faries et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 6,967,575 B1 | 11/2005 | Dohrmann et al. |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries et al. |
| 7,176,030 B2 | 2/2007 | Faries, Jr. et al. |
| 7,238,171 B2 | 7/2007 | Faries, Jr. et al. |
| 7,262,698 B1 | 8/2007 | Frederick et al. |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 7,540,864 B2 | 6/2009 | Faries et al. |
| 7,608,460 B2 | 10/2009 | Reed et al. |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries, Jr. et al. |
| 8,444,599 B2 | 5/2013 | Faries, Jr. et al. |
| 8,636,691 B2 | 1/2014 | Faries, Jr. et al. |
| 8,734,404 B2 | 5/2014 | Faries, Jr. |
| 8,734,405 B2 | 5/2014 | Faries, Jr. |
| 8,821,011 B2 | 9/2014 | Faries, Jr. et al. |
| 2001/0009610 A1 | 7/2001 | Augustine et al. |
| 2002/0041621 A1 | 4/2002 | Faries, Jr. et al. |
| 2002/0081109 A1 | 6/2002 | Mitsunaga et al. |
| 2002/0147426 A1 | 10/2002 | Faries, Jr. et al. |
| 2002/0151854 A1 | 10/2002 | Duchon et al. |
| 2002/0156451 A1 | 10/2002 | Lenker |
| 2002/0158058 A1 | 10/2002 | Faries, Jr. et al. |
| 2002/0184906 A1 | 12/2002 | Faries, Jr. et al. |
| 2003/0000939 A1 | 1/2003 | Faries et al. |
| 2003/0004470 A1 | 1/2003 | Hickerson et al. |
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0222933 A1 | 12/2003 | Choi |
| 2003/0231990 A1 | 12/2003 | Faries, Jr. et al. |
| 2004/0170409 A1 | 9/2004 | Faries, Jr. et al. |
| 2004/0189258 A1 | 9/2004 | Lehmann et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0242930 A1 | 11/2005 | Nicolson et al. |
| 2006/0020255 A1 | 1/2006 | Cassidy et al. |
| 2006/0100578 A1 | 5/2006 | Lieberman |
| 2006/0253075 A1 | 11/2006 | Faries, Jr. et al. |
| 2007/0000910 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0215018 A1 | 9/2007 | Faries, Jr. et al. |
| 2008/0021392 A1 | 1/2008 | Lurvey et al. |
| 2008/0058697 A1 | 3/2008 | Kamen et al. |
| 2008/0147016 A1 | 6/2008 | Faries et al. |
| 2008/0205481 A1 | 8/2008 | Faries et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2012/0053518 A1 | 3/2012 | Faries, Jr. et al. |
| 2012/0191050 A1 | 7/2012 | Faries, Jr. |
| 2012/0285236 A1 | 11/2012 | Haartsen et al. |

(56) References Cited

U.S. PATENT DOCUMENTS

| | | |
|---|---|---|
| 2013/0197437 A1 | 8/2013 | Faries et al. |
| 2014/0231406 A1 | 8/2014 | Tsang et al. |
| 2014/0236615 A1 | 8/2014 | Ragusky et al. |

FOREIGN PATENT DOCUMENTS

| | | |
|---|---|---|
| DE | 19752578 | 6/1999 |
| FR | 2711393 | 4/1995 |
| FR | 2786057 | 5/2000 |
| GB | 2029677 A | 3/1980 |
| GB | 2274514 | 7/1994 |
| JP | 58030666 | 2/1983 |
| JP | 2000300666 | 10/2000 |
| WO | 9221272 | 12/1992 |
| WO | WO 98/38953 | 9/1998 |
| WO | 9845658 | 10/1998 |
| WO | WO 99/22786 | 5/1999 |
| WO | WO 99/26690 | 6/1999 |
| WO | WO 99/58177 | 11/1999 |

OTHER PUBLICATIONS

Minco Products, Inc., *Bulletin CTI1998*, 1996.
Eurotherm Controls, Inc., *Model 2116 Temperature Controller*, 1997.
Ellenwood, *Drop Detector*, IBM Technical Bulletin, vol. 12, No. 5, Oct. 1969.
CBi Medical, Inc., *IV Fluid Warmer Model 8362*, 1992.
Cahill, *New Name, New Helmsman*, JEMS, Aug. 1996.
CBi Healthcare Systems, Inc., *Controlled Temperature Cabinet System*, JEMS, Mar. 1997.
Koolatron, *P-34 PC-3 Precision Control Thermoelectric Cooler/Warmer*, Jan. 1998.
Koolatron, *Canadian company announces the release of a precision control unit*, Aug. 1997.
Anton, *500 miles from nowhere, it'll give you a cold drink or a warm burger. . .* , Technology Update, 1993.
Koolatron, *1997 U.S. $ Price List*, 1997.
Kellow et al, *Drug Adulteration in Prehospital Emergency Medical Services*, Oct. 1994.

\* cited by examiner

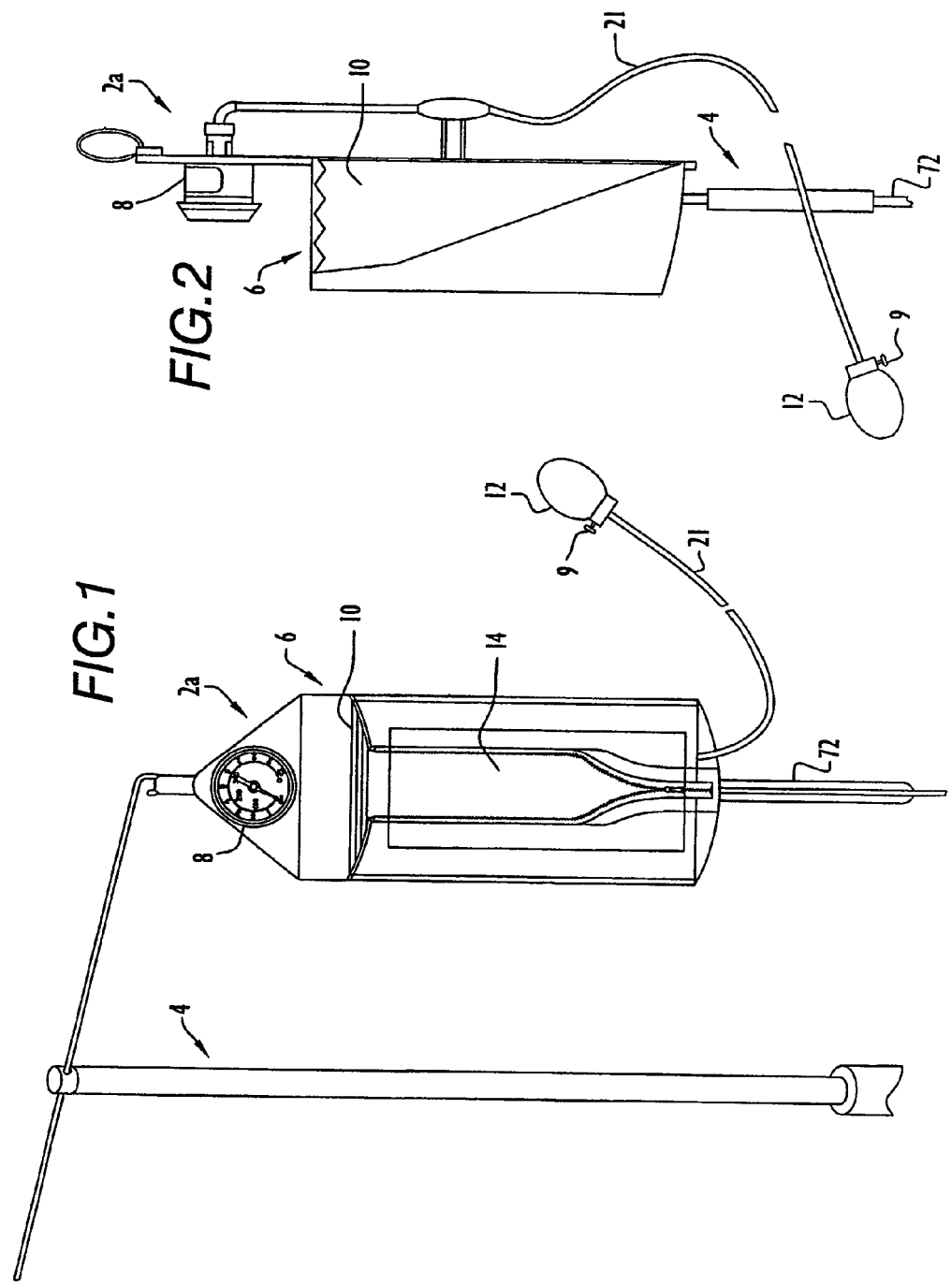

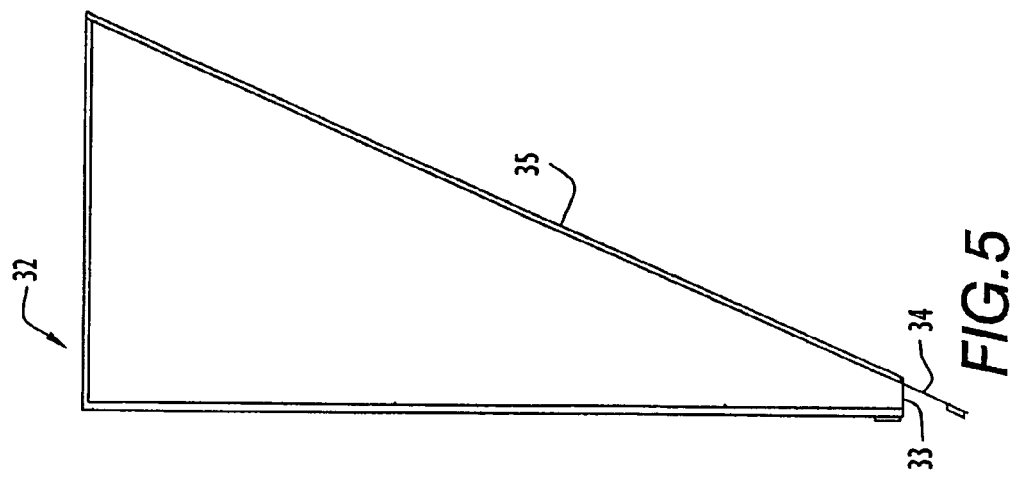
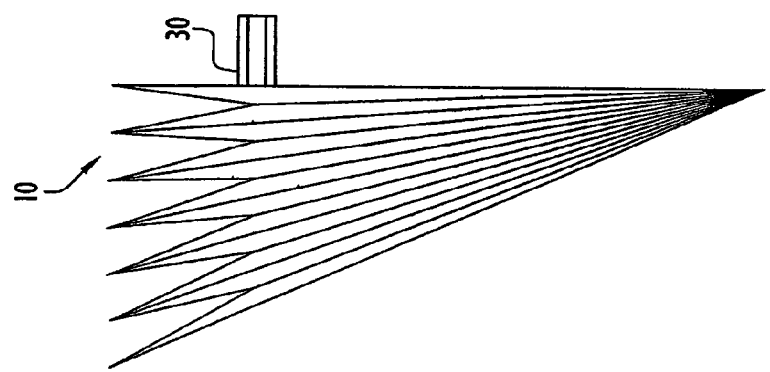
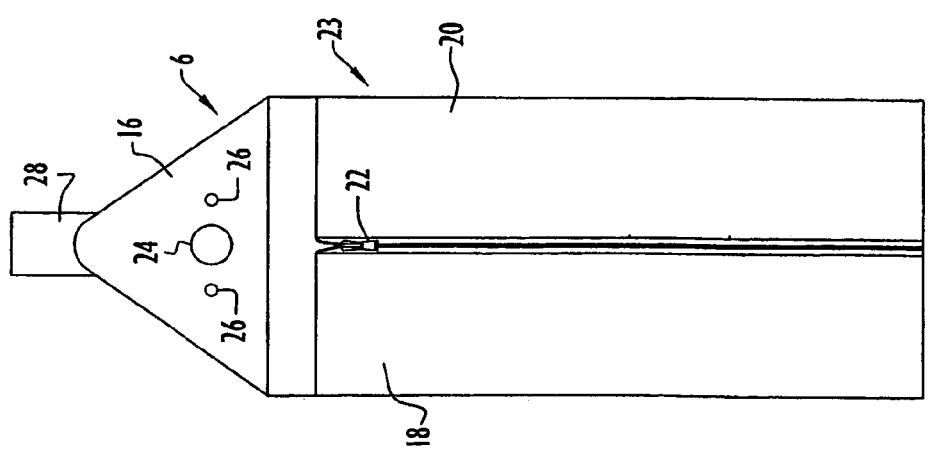

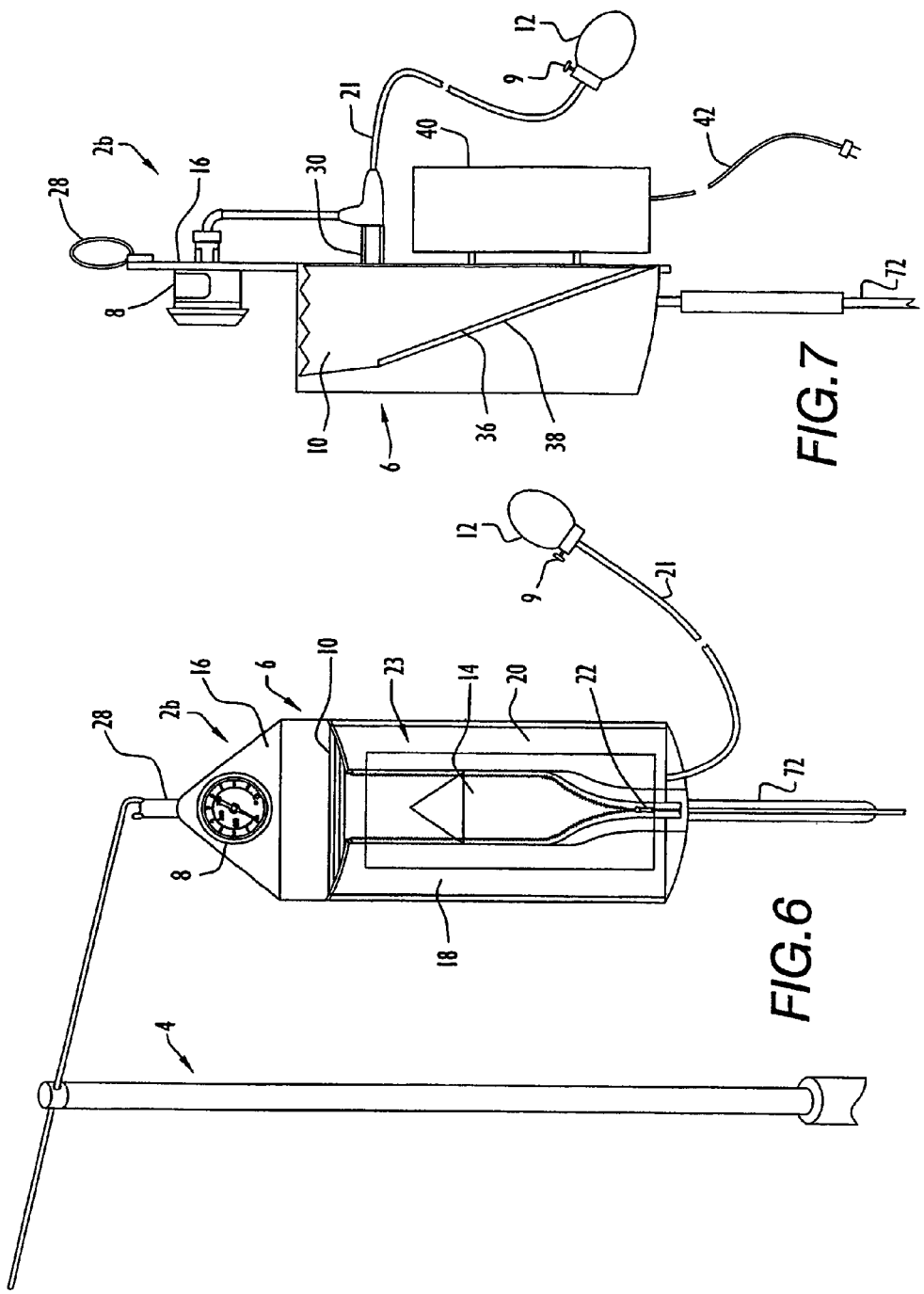

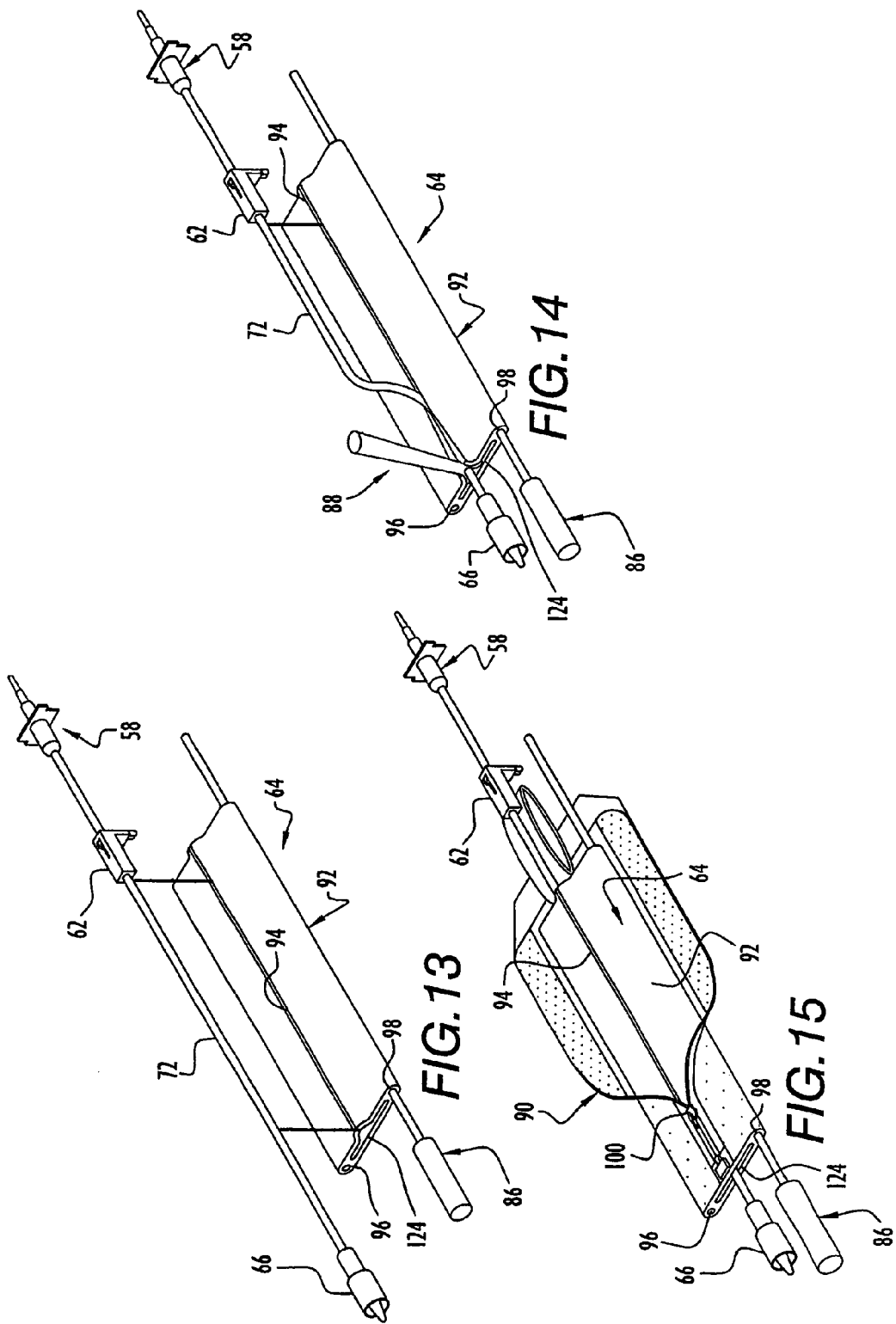

METHOD AND APPARATUS FOR PRESSURE INFUSION AND TEMPERATURE CONTROL OF INFUSED LIQUIDS

CROSS REFERENCE TO RELATED APPLICATIONS

This application is a divisional of U.S. patent application Ser. No. 10/913,512, now U.S. Pat. No. 7,942,851, entitled "Method and Apparatus for Pressure Infusion and Temperature Control of Infused Liquids" and filed Aug. 9, 2004, which is a continuation of U.S. patent application Ser. No. 09/380,507, filed Apr. 24, 2000, entitled "Method and Apparatus for Pressure Infusion and Temperature Control of Infused Liquids", now U.S. Pat. No. 6,824,528, which is a National Stage Application of PCT International Application No. PCT/US98/04199, filed Mar. 3, 1998, entitled "Method and Apparatus for Pressure Infusion and Temperature Control of Infused Liquids", which claims priority from U.S. Provisional Patent Application Ser. No. 60/040,885, filed Mar. 3, 1997, entitled "Method and Apparatus for Measurement and Control of Temperature for Infused Liquids", and U.S. Provisional Patent Application Ser. No. 60/062,315, filed Oct. 17, 1997, entitled "Method and Apparatus for Pressure Infusion and Temperature Control of Infused Liquids". The disclosures of the above-identified patent and patent applications are incorporated herein by reference in their entireties.

BACKGROUND OF THE INVENTION

1. Technical Field

The present invention pertains to pressurized infusion and temperature control apparatus or systems for infused liquids. In particular, the present invention is directed toward pressurized infusion of liquids into a patient and/or temperature control of that liquid during infusion into a patient.

2. Discussion of Prior Art

Generally, intravenous (I.V.) solution or other liquids are infused into a patient by disposing a liquid-filled bag containing intravenous solution or other liquid on a pole structure to permit gravitational forces to direct liquid from the liquid-filled bag through an intravenous or other tube into the patient. However, gravitational forces may be insufficient to drive certain viscous liquids, such as refrigerated blood, into the patient, or drive liquids into the patient at a sufficient rate. The prior art has attempted to overcome the aforementioned inadequacies of gravitational forces by applying pressure to the liquid-filled bag to enhance liquid flow from the liquid-filled bag to the patient. For example, U.S. Pat. No. 4,090,514 (Hinck et al) discloses a pressure infusion device including a bladder wherein the device encases a liquid-filled bag with the bladder surrounding at least eighty percent of that bag. Upon inflation of the bladder, liquid within the liquid-filled bag is infused under pressure to a patient. Further, U.S. Pat. No. 4,551,136 (Mandl) discloses a pressure infuser including an inflatable bladder that wraps about a liquid-filled bag. The bladder includes a vertical strip at each end and a strap that wraps about the bladder and liquid-filled bag. The vertical strips overlap to provide a complete wrap about the liquid-filled bag, while the strap maintains the overlapping strip portions in contact. The bladder is inflated to a desired pressure whereby pressure is applied by the bladder to the liquid-filled bag to infuse liquid into a patient.

The Hinck et al and Mandl devices suffer from several disadvantages. In particular, the Hinck et al device includes a bladder that substantially surrounds a liquid-filled bag, however, the bladder may not expand sufficiently to apply adequate pressure to the liquid-filled bag when small volumes of liquid are present within the liquid-filled bag, thereby operating less efficiently when smaller volumes of liquid reside within the liquid-filled bag and requiring premature replacement of the liquid-filled bag prior to utilization of liquid within that bag. Similarly, the Mandl infuser utilizes a strap to maintain a bladder about a liquid-filled bag wherein pressure exerted by the bladder on the liquid-filled bag is focused substantially coincident the strap, thereby operating less efficiently, especially when smaller volumes of liquid reside within the liquid-filled bag, since various pressures are applied to different portions of the liquid-filled bag (e.g., the bladder portions disposed near the strap apply the greatest amounts of pressure, while the bladder portions disposed furthest from the strap apply the least amounts of pressure), and requiring premature replacement of the liquid-filled bag prior to utilization of liquid within that bag. In other words, when the liquid-filled bags become partially depleted and thin, the bladders of the Hinck et al and Mandl devices may not maintain adequate pressure on the thinner bags for infusion of liquid into a patient. Further, the bladders of these devices generally include certain dimensions, thereby only being compatible or satisfactorily operable with liquid-filled bags of a particular size. Moreover, the Hinck et al and Mandl devices do not thermally treat the liquid-filled bags in any manner during infusion.

In addition to providing pressurized infusion as described above, it is desirable during surgical procedures to maintain a patient's body temperature at approximately 98.6° F. or 37° C. (i.e., normal body temperature) to avoid hypothermia and complications that may arise with minute decreases in body temperature (e.g., decreases of approximately 2-3° C.). Further, infusion into a patient of liquids having temperatures below the normal body temperature may produce further complications, such as shock, cardiac dysfunction, increased coagulation time, and in certain patients, clumping of blood cells.

In order to avoid hypothermia and other complications described above, warmers are typically employed during surgical or other medical procedures to maintain the temperature of infused liquids at or near body temperature. Generally, prior art warmer systems employ various techniques to heat infused liquids. In particular, infused liquid may be directed within tubing or a bag through a solution bath (e.g., warmed liquid); infused liquid may be directed about a tube through which warmer liquid flows in an opposing direction; infused liquid may traverse tubing or be stored in a bag placed proximate heating plates; infused liquid may be disposed in a bag placed about a heating element; infused liquid may be warmed by a heat exchanger in the form of a cassette placed between heating plates; or infused liquid may be warmed via heated air or microwave energy. For example, U.S. Pat. No. 1,390,500 (Christian) discloses a flexible water heater and dripper wherein water and other liquid flow from a container and are heated while traversing a flexible heating element having a conduit. The heating element includes resistance coils and is connected to a rheostat having a sliding member to control current to the heating device to provide a desired degree of heat.

U.S. Pat. No. 1,726,212 (Bucky) discloses an irrigator including a container filled with liquid having a heater for heating the liquid to a desired temperature. A bulb pumps air into the container to produce a pressure that drives the liquid through tubing to an irrigation site.

U.S. Pat. No. 1,995,302 (Goldstein) discloses an adjustable heating infusion apparatus wherein a flexible tube conveying fluid is heated via an electric resistance wire spirally wound about the tube outer surface. The wire spirals are more concentrated at a tube proximal end to raise liquid temperature toward a desired level, while the remaining windings maintain the liquid temperature at substantially that desired level. A thermostatic current control regulates current to the resistance wire to maintain a predetermined temperature.

U.S. Pat. No. 3,247,851 (Seibert) discloses an apparatus for applying liquids to the body wherein a heating unit extends along a length of a tube to heat liquid as the liquid flows from a receptacle. The heating unit includes heating wires and a thermostat to heat the liquid in the tube.

U.S. Pat. No. 5,250,032 (Carter, Jr. et al) discloses a heater for in vivo blood infusion including a housing having a channel for receiving a portion of an intravenous tube. A heating element is mounted proximate a slot disposed within the channel to heat the tube wherein the heating element is controlled by a control circuit and powered by batteries. The control circuit controls the heating element in response to sensed temperatures.

U.S. Pat. No. 5,254,094 (Starkey et al) discloses a physiological fluid warmer including two chambers having coils for fluid to flow, while a warming liquid flows through the chambers along the coils in a direction opposite to the fluid flow. The fluid warmer may be controlled by a microprocessor to operate in response to either fluid or warming liquid temperature.

The prior art warmer systems described above suffer from several disadvantages. In particular, the prior art warmer systems heating liquid within an intravenous or other tube tend to employ and control a single heating element disposed along the tube, thereby limiting control accuracy of the liquid temperature and typically producing hot spots (e.g., certain sections of the tube may become warmer than other sections of the tube). Some of the prior art warmer systems require pre-heating of a liquid-filled bag prior to use in and external of those systems, thereby requiring additional time to heat the liquid. Further, the prior art warmer systems heating liquid within an intravenous or other tube typically rely on gravitational forces to direct the liquid to the patient. These gravitational forces may be inadequate to produce desired flow rates or enable flow of viscous solutions as described above. Moreover, certain prior art warmer systems heat liquid flowing within an intravenous or other tube at a site located a substantial distance from the patient entry point, thereby permitting heated liquid to cool by the time the heated liquid reaches the patient. In addition, the prior art warmer systems typically control liquid heating based solely on temperature measurements of the liquid, thereby limiting control options and providing for less accurate control. The prior art warmer systems typically maintain activation of heating elements in cases of excessive liquid or heating element temperatures or interruptions in liquid flow, thereby enabling the heating elements to heat the liquid to temperatures beyond the liquid utilization temperature range and possibly injure a patient and/or damage an intravenous or other tube. A further disadvantage of the prior art warmer systems heating liquid within an intravenous or other tube is that the temperature of liquid contained within a liquid-filled bag or receptacle is typically substantially below a desired temperature, thereby requiring significant heating of the liquid during infusion as the liquid traverses the tube.

OBJECTS AND SUMMARY OF THE INVENTION

Accordingly, it is an object of the present invention to infuse liquid under pressure into a patient by exerting pressure in a downward fashion on a liquid-filled bag until virtually all of the liquid is spent.

It is another object of the present invention to infuse heated liquid under pressure into a patient.

Yet another object of the present invention is to control temperature of infused liquid via multiple individually controlled heaters disposed along an intravenous or other tube.

Still another object of the present invention is to control temperature of infused liquid flowing in an intravenous or other tube based on temperature and flow rate of the infused liquid.

A further object of the present invention is to control temperature of infused liquid by heating a liquid-filled bag or receptacle to a desired temperature and maintaining liquid from the liquid-filled bag at that temperature during infusion into a patient via a heater disposed along an intravenous or other tube.

The aforesaid objects are achieved individually and in combination, and it is not intended that the present invention be construed as requiring two or more of the objects to be combined unless expressly required by the claims attached hereto.

According to the present invention, a method and apparatus for pressure infusion and temperature control of infused liquids includes a receptacle for receiving a liquid-filled bag containing intravenous solution or other liquid and an inflatable pressure device or bellows. The bellows is disposed within a bellows bag and is positioned proximate the liquid-filled bag in the receptacle. The receptacle is typically suspended from an intravenous pole or other structure. A conventional bulb is manipulated to inflate the bellows wherein the bellows expands within the bellows bag upon inflation and exerts pressure on the liquid-filled bag to direct liquid from the liquid-filled bag through an intravenous or other tube to a patient. Further, the bellows bag includes a pocket that may receive a heating element and conductive plate to enable pressurized infusion of heated liquid into a patient. The heating element heats the liquid-filled bag to a desired temperature through the conductive plate, while the bellows exerts pressure on the liquid-filled bag to direct heated liquid from the liquid-filled bag to the patient in substantially the same manner described above.

Intravenous solution or other liquid may be maintained at a desired temperature during infusion via a heating assembly disposed along an intravenous or other tube. The tube extends to a patient entry site from a drip chamber that is coupled to a liquid-filled bag containing intravenous solution or other liquid. The liquid-filled bag is typically suspended from an intravenous pole or other structure. The heating assembly includes a sleeve having a substantially centrally disposed slot for receiving a portion of the tube and a plurality of individually controlled heaters located proximate the slot. The tube portion is typically inserted into the slot via a special tool, while the sleeve is disposed within a jacket. An infrared sensing device is mounted proximate the drip chamber to ascertain a drip count rate or, in other words, a liquid flow rate wherein a heat controller controls the heaters based on the drip count rate. In addition, a temperature sensor is disposed within a thermocouple holder that is positioned toward the entry site on the patient. The thermocouple holder positions the temperature sensor proximate the tube to obtain an accurate temperature measurement of the liquid near the entry site. A temperature signal is sent from the temperature sensor to an additional safety controller that displays the liquid temperature and disables the heaters in response to the liquid temperature being equal to or exceeding the desired temperature. Thus, the safety controller and heat controller, in combination, control the heating assembly heaters to maintain the liquid temperature substantially at the desired temperature based on liquid temperature and flow rate, respectively, wherein disablement of the heating assembly heaters by the safety controller overrides any heater controls given by the heat controller. Alternatively, the liquid-filled bag may be heated to a desired temperature and the heating assembly sleeve may contain a single heater controlled by a controller to maintain the liquid at the desired temperature during infusion of the liquid into a patient.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 1 is a view in perspective of a pressurized infusion system according to the present invention.

FIG. 2 is a side view in elevation of the pressurized infusion system of FIG. 1.

FIG. 3 is a front view in elevation of a receptacle of the pressurized infusion system of FIG. 1 for containing a liquid-filled bag and a bellows disposed within a bellows bag.

FIG. 4 is a side view in elevation of a bellows of the pressurized infusion system of FIG. 1.

FIG. 5 is a side view in elevation of a bellows bag for containing the bellows of FIG. 4.

FIG. 6 is a view in perspective of a pressurized infusion system that heats infused liquids according to another embodiment of the present invention.

FIG. 7 is a side view in elevation of the pressurized infusion system of FIG. 6.

FIG. 13 is an exploded view in perspective of a heating assembly of the temperature control system of FIG. 11 receiving a portion of an intravenous or other tube.

FIG. 14 is an exploded view in perspective of a portion of an intravenous or other tube inserted within the heating assembly of FIG. 13 via a tool.

FIG. 15 is a view in perspective of the heating assembly of FIG. 13 encased within a jacket.

DESCRIPTION OF THE PREFERRED EMBODIMENTS

Figure 16:
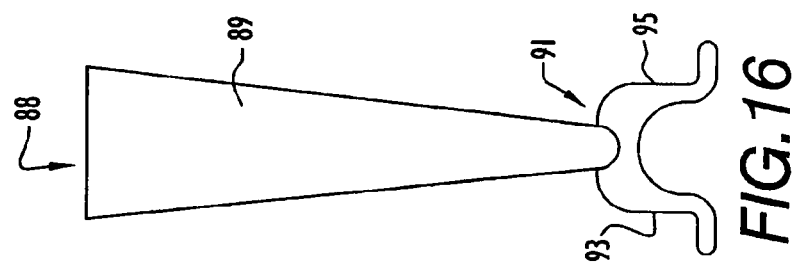
FIG. 16 is a view in elevation of the tool of FIG. 14 for inserting a portion of an intravenous or other tube within the heating assembly of FIG. 13.

A pressurized infusion apparatus or system for irrigating a patient or directing infused liquids into a patient is illustrated in FIGS. 1-2. Specifically, system 2a is typically mounted on a conventional intravenous (I.V.) pole 4 and includes a receptacle 6 for containing intravenous solution or other liquid and engaging pole 4, a pressure gauge 8, an inflatable pressure device or bellows 10, a bulb 12 for regulating fluid pressure within the bellows via a hose 21, and an intravenous or other tube 72 for directing liquid from the receptacle to a patient. Receptacle 6 typically receives a liquid-filled bag 14 (e.g., a bag containing intravenous solution or other liquid) and bellows 10 wherein the bellows is disposed within a bellows bag 32 (FIG. 5) and positioned adjacent the liquid-filled bag. Hose 21 extends between bellows 10 and bulb 12 wherein manipulation of the bulb drives fluid into or from the bellows through hose 21. Hose 21 is typically implemented by a conventional or other type of hose, may be of any size or shape and may be constructed of any suitable materials. Inflation of bellows 10 via bulb 12 enables the bellows to expand within bellows bag 32 and apply pressure to liquid-filled bag 14, thereby driving liquid from the liquid-filled bag through tube 72 to a patient. Bulb 12 includes a valve 9 to release fluid from bellows 10 such that the bulb may add or reduce pressure applied by the bellows to liquid-filled bag 14 based on pressure levels within the bellows indicated by pressure gauge 8. For example, increased fluid pressure within the bellows increases pressure exerted by the bellows onto the liquid-filled bag, while decreased fluid pressure within the bellows reduces pressure exerted by the bellows onto the liquid-filled bag. Pressure gauge 8 may be implemented by any conventional or other type of pressure gauge or device, and provides a measurement and indication of fluid pressure within the bellows produced by manipulation of bulb 12. The bellows and bellows bag each include a substantially triangular or wedge shape and are typically disposed in receptacle 6 with their respective portions having the greatest thickness positioned toward the upper portion of liquid-filled bag 14. However, the bellows and bellows bag may be of any shape or size, while the bellows may be implemented by any device capable of applying pressure to the liquid-filled bag. Pressure is applied by bellows 10 to liquid-filled bag 14 in a downward manner to drive the liquid downward, to control the flow rate of the liquid and to produce an even flow. It is to be understood that the terms "upper", "lower", "up", "down", "front", "back", "rear", "top", "bottom", "side", "left", "right", "far", "near", "height", "width", "thickness" and "length" are used herein merely to describe points of reference and do not limit the present invention to any particular configuration or orientation.

Referring to FIG. 3, receptacle 6 includes a compartment or storage area 23 and a generally triangular projection 16 extending from the upper portion of the compartment to engage pole 4 (FIGS. 1-2). The compartment is in the form of a substantially rectangular bag having an open top portion and includes dimensions greater than the combined dimensions of liquid-filled bag 14 and bellows bag 32 (i.e., containing bellows 10) in order to receive these items. The front portion of compartment 23 includes strips 18, 20 that are fastened together via a zipper 22 or any other fastening device. Zipper 22 is typically implemented by a conventional zipper and generally extends along a substantially central longitudinal axis of the compartment front portion to fasten an edge of strip 18 to an adjacent or facing edge of strip 20. The zipper enables the compartment front portion to be substantially closed to maintain bellows bag 32 (i.e., containing bellows 10) and liquid-filled bag 14 within the compartment. In other words, zipper 22 essentially enables placement and removal of the bellows bag (i.e., containing the bellows) and liquid-filled bag within the compartment. The zipper or other fastening device may be disposed anywhere on the compartment in any fashion to facilitate placement and removal of items within the compartment. The compartment rear portion typically includes an opening (not shown) to permit fluid transfer between bulb 12 and bellows 10 via hose 21 (FIG. 2). The opening may be of any size or shape capable of permitting the hose to extend to the bellows.

Generally triangular projection 16 extends from the upper back portion of compartment 23 and includes openings 24, 26 and a loop 28. Openings 24, 26 are defined toward the projection center with opening 24 disposed between openings 26. These openings enable pressure gauge 8 (FIGS. 1-2) to be mounted on the receptacle. Loop 28 is disposed toward the upper portion of a rear exterior surface of the projection to engage pole 4 and to enable receptacle 6 to be attached to the pole. The receptacle houses the liquid-filled bag and bellows bag (i.e. containing the bellows) to produce pressurized infusion of liquids as described above. The compartment, projection and loop may be of any size or shape, and may be constructed of plastic, rubber or any other suitable materials. By way of example only, the compartment has a height of approximately ten inches and a width of approximately nine inches, while the projection extends approximately three inches from the compartment with the loop extending approximately one inch from the projection.

Bellows 10 for driving liquid from liquid-filled bag 14 to a patient is illustrated in FIG. 4. Specifically, bellows 10 is generally right triangular and in the form of a wedge. The bellows may be of any size or shape, may be constructed of plastic, rubber, fabric or any other suitable materials, and may be implemented by any conventional or other type of expandable device. By way of example only, the bellows has a height of approximately nine inches, a width of approximately four and one-half inches and an uninflated thickness of approximately four inches (i.e., the thickness varies depending on the amount of inflation). The upper portion and sides of the bellows typically include a series of peaks and recesses in a sawtooth configuration extending between front and rear surfaces of the bellows similar in structure to an accordion. An inlet or port 30 is disposed on a rear exterior surface of the bellows to permit fluid to flow into and from the bellows. The port is typically connected to bulb 12 via hose 21 (FIGS. 1-2), and may be of any size or shape and disposed anywhere on the bellows. When bulb 12 is manipulated to drive fluid into bellows 10, the bellows expands laterally and downward within bellows bag 32 (FIG. 5) and applies pressure to liquid-filled bag 14 to drive liquid to a patient as described above.

Bellows 10 is disposed within bellows bag 32 and is positioned in receptacle 6 adjacent liquid-filled bag 14 as described above wherein bellows bag 32 for housing the bellows is illustrated in FIG. 5. Specifically, bellows bag 32 is generally right triangular in the form of a wedge with a front tilted surface and includes dimensions greater than the dimensions of bellows 10 to accommodate the bellows in an expanded or compressed state. The bellows bag is typically constructed of cordura nylon, however, the bellows bag may be constructed of any fabric or suitable materials. Bellows bag 32 includes an opening 33 disposed at the bellows bottom for insertion of the bellows into the bellows bag. A flap 34 is disposed proximate opening 33 and extends from the bottom portion of the bellows bag to cover opening 33 and to maintain the bellows within the bellows bag. Further, a port opening (not shown) may be defined in the bellows bag rear surface to enable fluid transfer between bellows 10 and bulb 12 (FIG. 2) via port 30 (FIG. 4) and hose 21 as described above. In addition, a pocket 35 may be disposed on the bellows bag front tilted surface for receiving a conductive plate and heating element to heat liquid-filled bag 14 (FIG. 6) as described below. The bellows bag may be of any size or shape and, by way of example only, includes a height of slightly greater than approximately nine inches, a width of slightly greater than approximately four and one-half inches and a depth of approximately three inches.

Operation of the pressurized infusion system is described with reference to FIGS. 1-5. Specifically, bellows 10 is disposed within bellows bag 32 and is placed along with liquid-filled bag 14 in receptacle 6. The receptacle is typically mounted on pole 4 via loop 28 as described above. Bellows bag 32 (i.e., containing bellows 10) is disposed proximate liquid-filled bag 14 such that liquid-filled bag 14 compresses the bellows within bellows bag 32. Bulb 12 is manipulated to direct fluid into bellows 10 through hose 21 to enable the bellows to expand within bellows bag 32 and exert pressure in a downward manner on liquid-filled bag 14 to drive liquid to a patient. Valve 9 may be manipulated to release pressure from the bellows as described above such that the pressure and flow rate of the liquid may be controlled. Pressure gauge 8 measures and displays the fluid pressure within bellows 10 produced by manipulation of the bulb, and upon reaching the desired pressure, liquid is driven from liquid-filled bag 14 to a patient at a certain flow rate.

Alternatively, system 2a may further include a heater or heating element to heat liquid-filled bag 14 for pressurized infusion of heated liquid into a patient as illustrated in FIGS. 6-7. Specifically, system 2b is substantially similar to system 2a described above except that system 2b heats liquid-filled bag 14 or maintains the temperature of a pre-heated liquid-filled bag for infusion of heated liquid into the patient. Bellows 10 is disposed within bellows bag 32 and is placed along with liquid-filled bag 14 in receptacle 6 as described above. Bellows bag 32 (i.e., containing bellows 10) is disposed adjacent liquid-filled bag 14 such that the bellows expands within the bellows bag via inflation by bulb 12 to exert pressure on liquid-filled bag 14 and drive liquid to a patient in substantially the same manner described above. A heater or heating element 36 and conductive plate 38 are disposed within pocket 35 of bellows bag 32 (FIG. 5) such that the heating element and conductive plate are located adjacent liquid-filled bag 14. Pocket 35 is typically formed on bellows bag 32 via additional material extending for a substantial portion of the bellows bag height and having a substantially central opening for permitting the conductive plate to apply heat from the heating element to liquid-filled bag 14. As bellows 10 is inflated, the bellows presses conductive plate 38 against liquid-filled bag 14 to heat the liquid contained within that bag. A substantially rectangular control box 40 is mounted on pole 4 and includes circuitry to control power supplied to heating element 36. Control box 40 typically receives power from a common wall outlet jack via power cord 42, and may be of any shape or size and may be constructed of any suitable materials.

Figure 8:
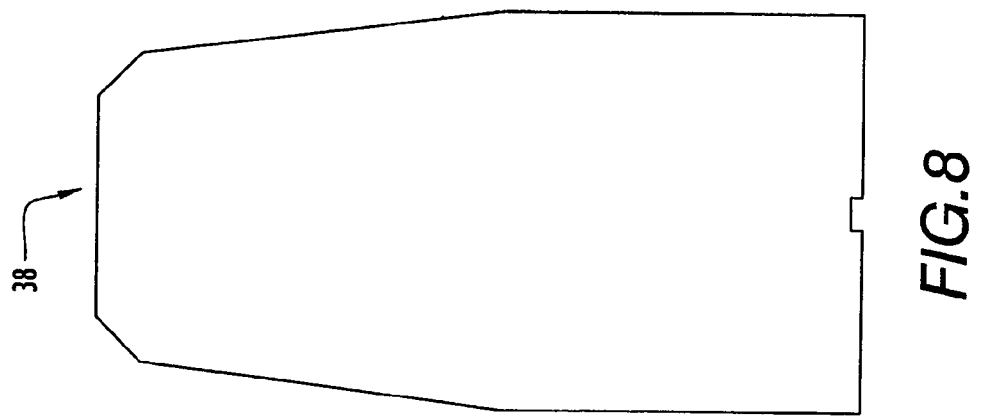
FIG. 8 is a view in elevation of a conductive plate of the pressurized infusion system of FIG. 6.

Referring to FIG. 8, conductive plate 38 is generally rectangular having a notch disposed at the approximate center of its bottom edge. The plate tapers slightly along its shorter dimension towards the upper portion of the plate and includes truncated or cut-off upper portion corners. By way of example only, the plate is constructed of copper and has a height of approximately eight and one-half inches and a width of approximately four and one-half inches, however, the plate may be constructed of any suitable conductor materials and may be of any size or shape. The conductive plate applies heat from heating element 36 (FIG. 7) to a substantial portion of liquid-filled bag 14.

Figure 9:
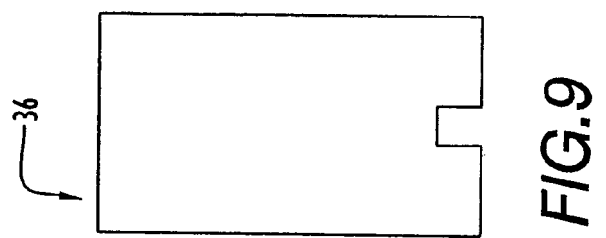
FIG. 9 is a view in elevation of a heating element of the pressurized infusion system of FIG. 6 for heating infused liquids.

Heating element 36 for applying heat to the liquid-filled bag through conductive plate 38 is illustrated in FIG. 9. In particular, the heating element is substantially rectangular and includes a notch disposed at the approximate center of its bottom edge. The heating element is disposed between the conductive plate and bellows bag to convey heat through the conductive plate to a substantial portion of the liquid-filled bag. By way of example only, heating element 36 is constructed of copper and includes a height of approximately four and one-quarter inches and a width of approximately two and one-half inches, however, the heating element may be constructed of any suitable conductor materials and may be of any size or shape.

Figure 10:
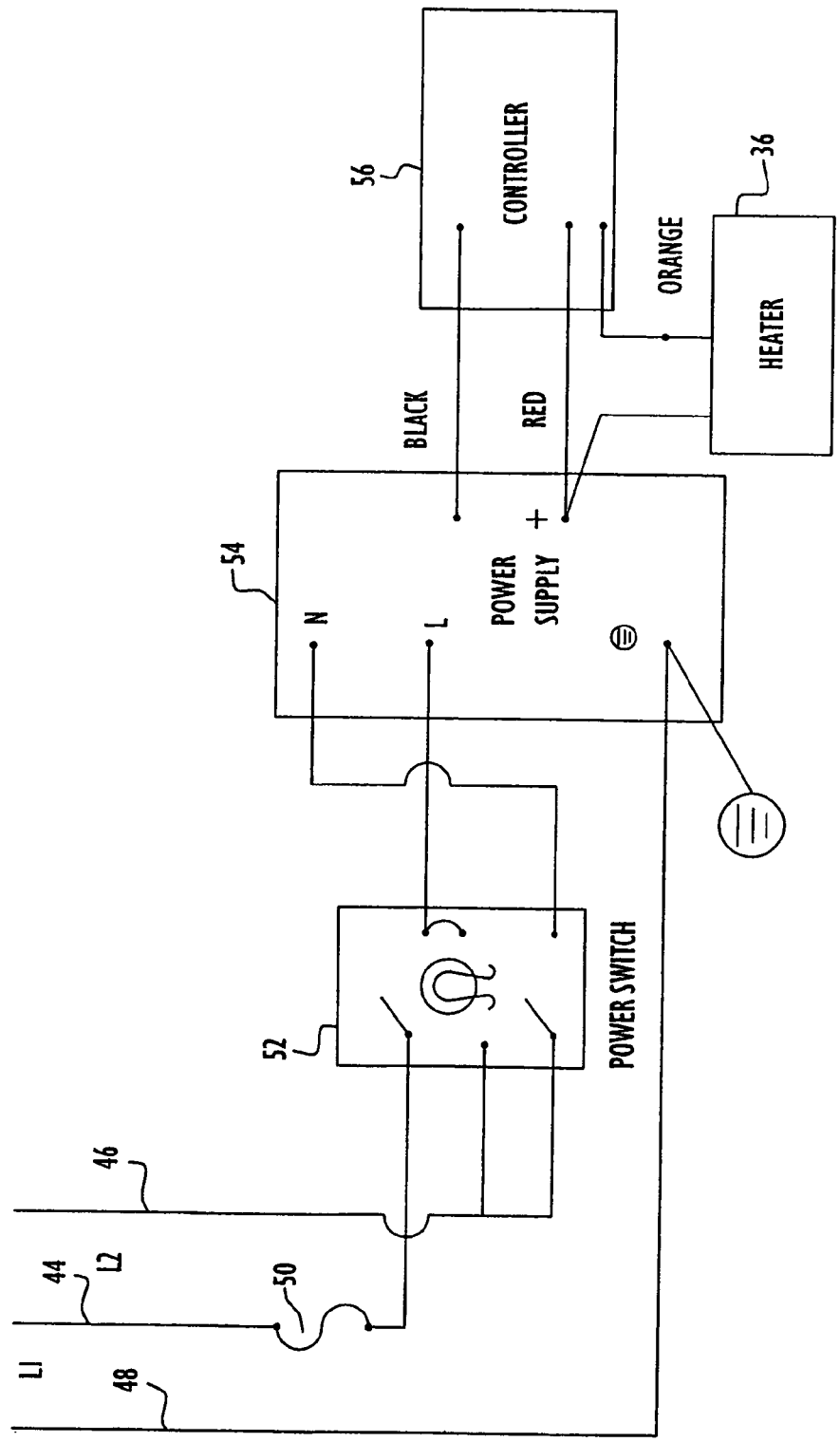
FIG. 10 is an electrical schematic diagram of an exemplary heater control circuit for the pressurized infusion system of FIG. 6.

A control circuit for controlling heating element 36 is illustrated in FIG. 10. Specifically, lines 44, 46 and 48 represent the power received from power cord 42 (FIG. 7) with line 48 connected to ground. Line 44 is connected in series with a fuse 50 to protect the circuit from power surges and spikes. Lines 44, 46 are connected to a power switch 52 that controls power to the circuit. The power switch enables a power supply 54 to provide power, typically up to a maximum of 24V, to heating element 36 via a controller 56. Controller 56 is connected to power supply 54 and heating element 36 to control power to the heating element based on a temperature measurement. Controller 56, in essence, includes both control circuitry and a sensor to control heating element 36 based on a predetermined temperature. The controller measures resistance through heating element 36, thereby providing a temperature indication. A predetermined resistance is programmed into controller 56 to provide a preset temperature wherein the controller compares the measured heating element resistance to the predetermined resistance to control the heating element. If the measured resistance is below the predetermined resistance (i.e., measured temperature is below the preset temperature), then controller 56 increases power to the heating element to increase heat and resistance. Conversely, if the measured resistance is above the predetermined resistance (i.e., measured temperature is above the preset temperature), controller 56 decreases power to the heating element to decrease heat and resistance. Thus, the controller maintains heating element 36 substantially at the predetermined resistance (i.e., temperature) by passing appropriate amounts of power to the heating element. The lines, power supply, heating element and controller may be implemented by any conventional components, however, by way of example only, controller 56 is implemented by a Minco CT-198 controller. The control circuitry is typically disposed within controller box 40 (FIG. 7) mounted on pole 4 described above.

Operation of the heating and pressurized infusion system is described with reference to FIGS. 6-10. Specifically, a temperature or resistance is preset into controller 56 as described above, while bellows 10 is disposed within bellows bag 32 and is placed along with liquid-filled bag 14 in receptacle 6. The receptacle is typically mounted on pole 4 as described above. Bulb 12 is manipulated to drive fluid into bellows 10 as described above wherein the bellows expands within the bellows bag and presses conductive plate 38, heated via heating element 36, against the liquid-filled bag, thereby heating the liquid-filled bag, controlling flow rate and driving liquid to a patient. The control circuit measures the resistance of heating element 36 and varies power to the heating element to maintain temperature of the heating element, and hence, the liquid-filled bag at the predetermined temperature. Alternatively, a pre-heated liquid-filled bag (e.g., heated to 100° F.) may be inserted within receptacle 6 adjacent bellows bag 32 (i.e., containing bellows 10). Heating element 36 may be controlled via controller 56 to maintain the pre-heated liquid-filled bag at the predetermined temperature, while the bulb and bellows may be used to control flow rate and drive liquid from the pre-heated liquid-filled bag to a patient in substantially the same manner described above.

Figure 11:
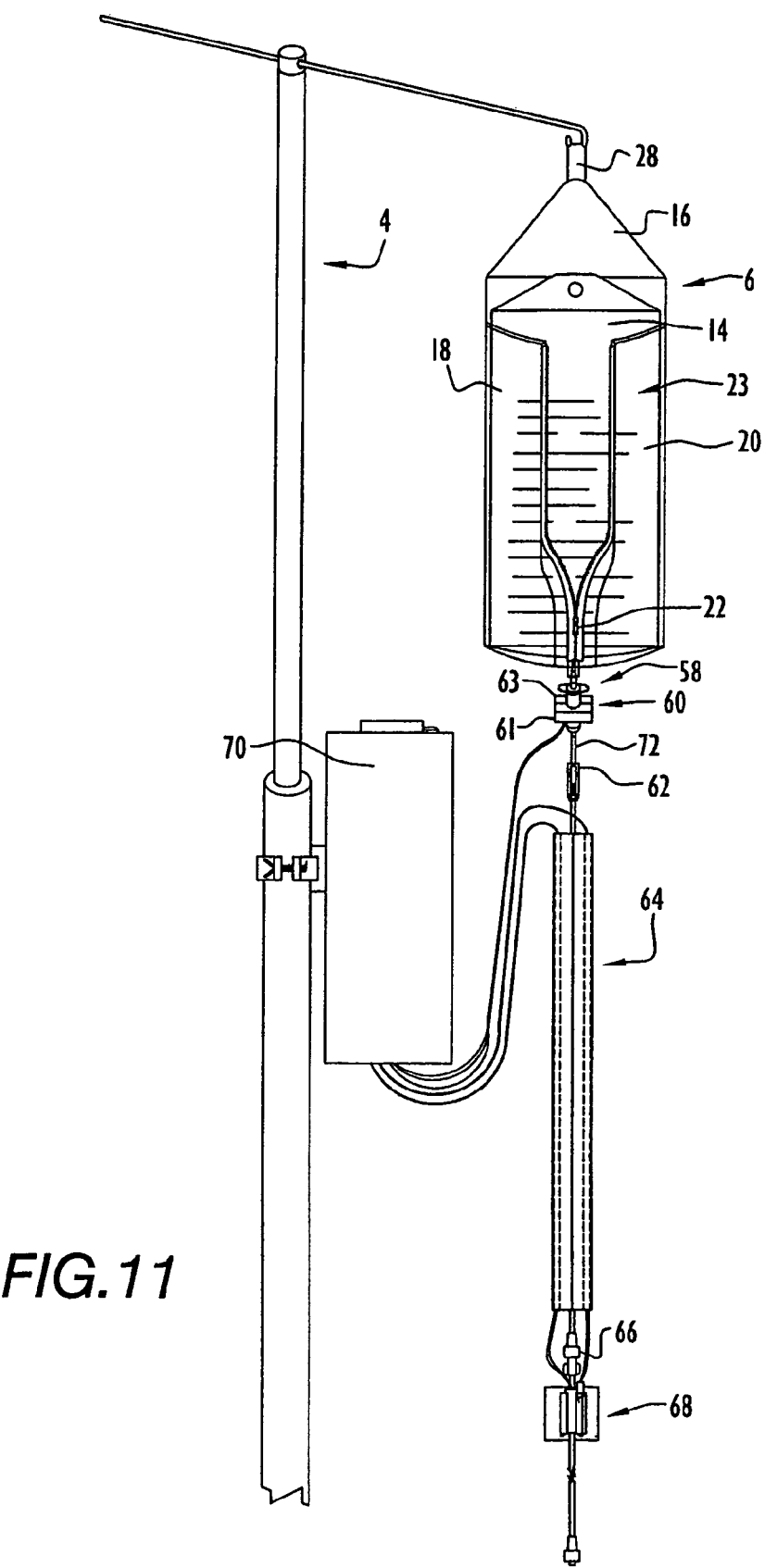
FIG. 11 is a view in perspective of a temperature control system for infused liquids according to yet another embodiment of the present invention.

A temperature control or warming system for heating liquid traversing an intravenous or other tube during irrigation or infusion is illustrated in FIG. 11. The temperature control system may be utilized in combination with the pressure infusion systems described above. An exemplary configuration includes receptacle 6, a drip chamber 58, a drip detector 60, an intravenous or other tube 72, a roller lock 62, a heating assembly 64, a connector 66 and a thermocouple holder 68. Receptacle 6 typically contains a liquid-filled bag 14, while being mounted on an intravenous (I.V.) pole 4. The receptacle may further include bellows 10 and bellows bag 32 (FIG. 5) with or without heating element 36 and conductive plate 38 as described above (FIGS. 2 and 7). Liquid flows from liquid-filled bag 14 to drip chamber 58 having drip detector 60 surrounding the drip chamber to detect each drip. Drip detector 60 typically employs an infrared emitter and several infrared detectors as described below to ensure accurate detection of drips. Tube 72 extends from drip chamber 58 wherein roller lock 62 is disposed on tube 72 subsequent the drip chamber to control fluid flow in the tube. After the roller lock, tube 72 traverses heating assembly 64, in the form of a sleeve having heaters disposed therein, to maintain the liquid at a predetermined temperature. Subsequent heating assembly 64, tube 72 traverses connector 66 (e.g., a Luer connector) and interfaces thermocouple holder 68. Thermocouple holder 68 maintains a temperature sensor, preferably an infrared sensor, in the proper position adjacent tube 72 to obtain an accurate temperature measurement of the liquid near an entry point on a patient. The thermocouple holder is typically attached to a patient's limb or body near the entry point via an approved medical biocompatible adhesive or any other techniques (e.g., tape). Following thermocouple holder 68, tube 72 extends to the entry point to infuse liquid into the patient via a needle or other medical device. A substantially rectangular control panel box 70 is mounted on pole 4 and controls system operation, while displaying the temperature and drip count to a user. The control panel box may be of any shape or size and may be constructed of any suitable materials.

Figure 12:
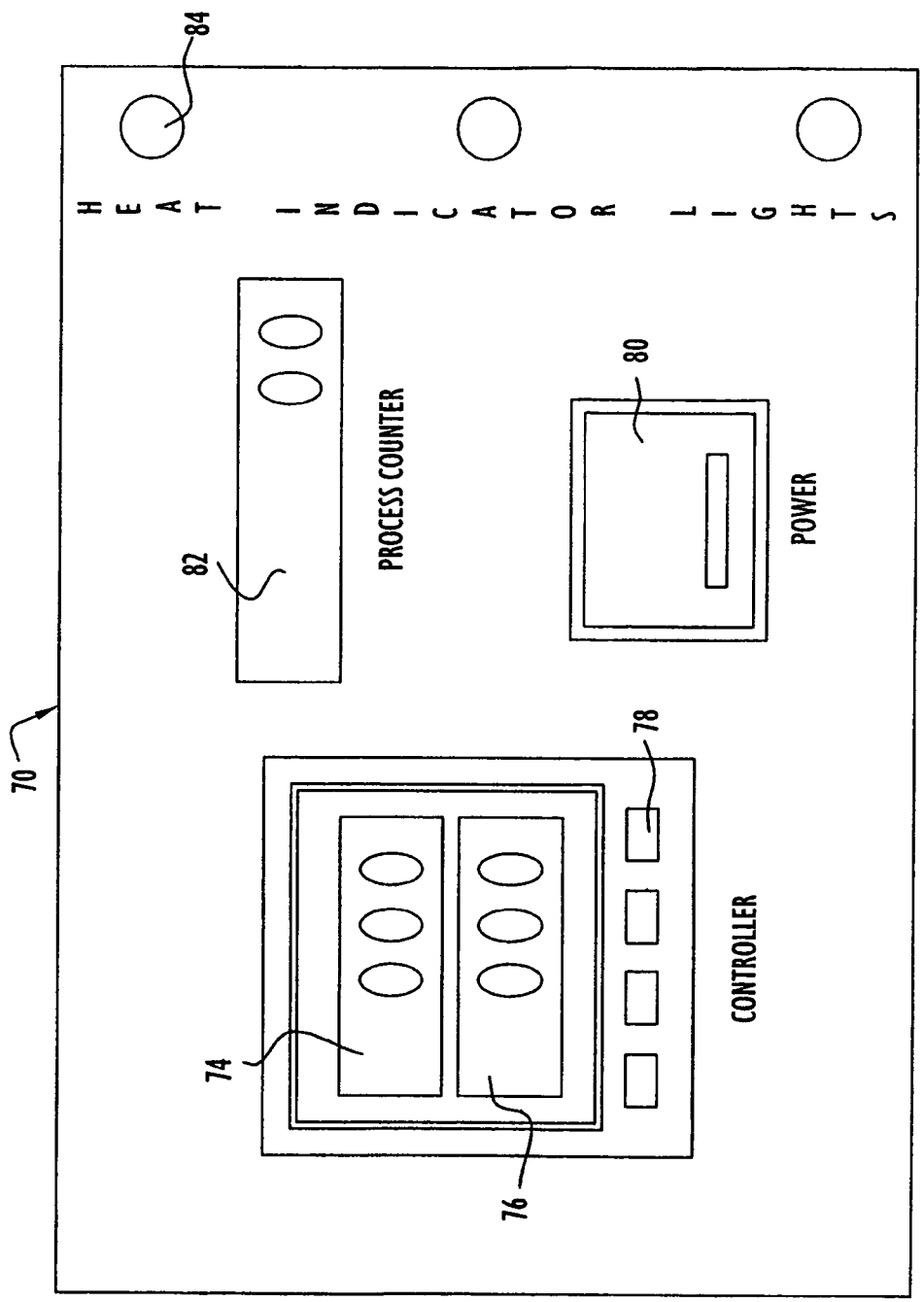
FIG. 12 is a front view in elevation of a control panel box of the temperature control system of FIG. 11.

Control panel box 70 displays various items and controls system operation as illustrated in FIG. 12. Specifically, control panel box 70 includes temperature display 74, set point (i.e., predetermined or desired temperature) display 76, controller program buttons 78, power switch 80, counter display 82 and heater indicator lights 84. Power switch 80 enables power to the system and is disposed at the approximate center of the lower portion of the control panel box front surface. Heater indicator lights 84 are substantially vertically aligned toward a far edge (e.g., rightmost edge as viewed in FIG. 12) of the control panel box front surface and are illuminated to indicate activation of the heaters, which heaters are activated, and the length of time a heater is activated in a cycle according to the drip rate. Temperature and set point displays 74, 76 are disposed toward the central portion of an edge (e.g., leftmost edge as viewed in FIG. 12) of the control panel box front surface opposing heater indicator lights 84 with temperature display 74 disposed above set point display 76. Temperature display 74 displays the liquid temperature as detected by a temperature sensor described below, while set point display 76 displays the predetermined or desired liquid temperature. Controller program buttons 78 are disposed below set point display 76 and enable the set point and other information to be programmed into a safety controller described below. The buttons typically include functions, such as up, down, scroll and page, to program and enter data into the controller. Counter display 82 is disposed above power switch 80 between temperature display 74 and indicator lights 84, and displays a count of the drips detected by drip detector 60 (FIG. 11) during a predetermined time interval. The counter display further indicates proper operation of drip detector 60 and may be utilized for system diagnostics. Additional displays may be included on the control panel box front surface to display total drip counts and total volume of liquid dispensed. The displays may be implemented by any conventional LED or LCD or other displays, while the lights and power switch may be implemented by any conventional components, such as diodes and switches, respectively. The control panel displays, lights and switches may be arranged in any fashion and disposed anywhere on the control panel box or on a separate panel.

Referring to FIGS. 13-15, heating assembly 64 typically includes an elongated sleeve 92 having a plurality of heaters 124 disposed therein to heat liquid in tube 72. Any quantity of sleeves or heating assemblies may be utilized by the system. Sleeve 92 includes a slot 94 extending longitudinally along an upper sleeve surface for receiving a portion of tube 72, and has a generally elliptical cross-section with channels 96, 98 defined through the sleeve for accommodating wiring. Typically, channels 96, 98 accommodate voltage wires extending from the heaters to prevent the heaters from heating or burning the wires. The plurality of heaters are disposed coincident the slot between channels 96, 98 such that the tube portion is disposed against the heaters to enable temperature control of liquid within the tube. Sleeve 92 is designed to secure the tube portion against the heaters and to provide insulation to protect the patient from burns. The heaters are typically manufactured by Watlow, but may be implemented by any conventional or other type of heater, for example, Kapton heaters. The tube portion is typically inserted within slot 94 via a tool 88 described below. A temperature sensor 86 is initially positioned external of heating assembly 64 with wires extending from the sensor to the control panel box. Channel 96 (e.g., the leftmost channel in FIGS. 13-15) typically accommodates wires extending between control panel box 70 and the heaters, while channel 98 (e.g., the rightmost channel in FIGS. 13-15) typically accommodates wires for temperature sensor 86. The tube portion is typically disposed in the heating assembly with temperature sensor 86 subsequently disposed within thermocouple holder 68 (FIG. 11) as described below. A jacket 90, typically constructed of canvas, encases heating assembly 64 and is closed via a zipper 100 that extends along substantially the entire length of sleeve 92 to protect users, patients and equipment from burns and to secure the heating sections of the assembly. Jacket 90 is typically placed over the heating assembly after placement of the tube portion and temperature sensor as described above. The sleeve may be constructed of plastic, silicon, rubber or any suitable materials and may be of any size or shape to accommodate various heaters and any sized tube portion from any type of tube.

Typically, heating assembly 64 includes three twenty watt, 120V heaters 124 individually controlled by a heat controller described below. However, any quantity or combination of heaters having various power characteristics may be utilized. For example, three forty watt heaters, or a forty watt and a twenty watt heater may be utilized in the heating assembly. Heaters 124 are each controlled, in part, by a heat controller or processor based on a count of drips detected, during a predetermined time interval, within drip chamber 58 (FIG. 11) via an infrared emitter and infrared detectors described below. In other words, the processor activates individual heaters based on liquid flow rate or the drip count. Heaters 124 each directly supply heat to tube 72 via heating assembly 64 as described above, and may be activated by the processor in any combination (e.g., a first heater may be activated, while a second heater is activated intermittently, all heaters may be activated or only a single heater may be activated) as described below. The processor controls each heater 124 based on a drip count by controlling line voltage to a solid state switching relay associated with that heater to activate that heater for a specified time interval and then deactivate the heater (i.e., the drip count determines which heaters to activate and the time interval for activation).

The utilization of multiple heaters 124 provides enhanced control, as compared to utilization of a single heater, for various flow ranges without burning tube 72. Further, the multiple heater arrangement avoids hot spots by selectively heating different portions of the tube. The temperature control system further includes a separate safety controller that disables heaters 124 in response to detecting temperatures equal to or above the predetermined or desired temperature. This avoids residual heat (e.g., heat applied to the tube after a malfunction or an interruption in the liquid flow) and prevents temperature change from reaching a patient. The disablement of heaters 124 by the safety controller overrides any heater controls issued by the heat controller. Thus, operation of heaters 124 is controlled by criteria empirically obtained based on measured drip count and temperature.

The system further includes various safety features to disable heaters 124 based on detection of certain events. For example, when the drip counter malfunctions, the temperature sensor becomes loose at the user end, the liquid-filled bag is tipped or relatively empty, the liquid temperature is equal to or exceeds a threshold temperature range (e.g., approximately 104-107° F.), or the liquid flow is interrupted, the system may disable the heaters.

Since the system heats the tube as needed at less than full power and intermittently (e.g., the safety controller disables the heaters in response to liquid temperature), the desired set point (i.e., temperature) is attained rapidly, while the liquid temperature drops rapidly at shut down (e.g., approximately 13° F. or more in a minute with reset occurring within one second). The safety controller may include an audible alarm for high and low temperatures that typically sounds prior to a patient feeling a temperature change. Further, an alarm may warn when a liquid-filled bag is at a low level. A change in drip size and/or density may affect the waveshape of the infrared detectors, thereby activating heaters less within a cycle, while the temperature decreases. The safety controller can sense this occurrence and provide an alarm giving advanced warning. Alternatively, two alarms may be utilized wherein a first alarm sounds in advance (e.g., during depletion of the liquid-filled bag) and a second alarm sounds when liquid is substantially spent from the liquid-filled bag. The phase down prevents heat residual within the tube.

Tool 88 for inserting a portion of tube 72 within slot 94 of sleeve 92 is illustrated in FIGS. 14 and 16. Specifically, tool 88 includes a handle 89 and tube interface 91. Handle 89 is disposed at the tool proximal end and is generally rectangular having a rounded distal end toward tube interface 91. Tube interface 91 is disposed at the handle distal end and includes legs 93, 95 each having a curved portion to form a generally semi-circular opening between the legs for receiving tube 72. However, the opening may be of any shape or size capable of receiving the tube. Legs 93, 95 each transversely extend in opposing directions from the distal end of their respective curved portion to engage slot 94 and facilitate placement of the tube portion within the heating assembly. The tool receives tube 72 in the opening between legs 93, 95, while the transverse portions of the legs penetrate slot 94 to place the tube portion snugly within the slot adjacent heaters 124 in order to enable the heaters to heat liquid within the tube. The tool may be constructed of aluminum or any other suitable materials and may be of any size or shape, however, by way of example only, the tool includes a height of approximately three inches.

Figure 18:
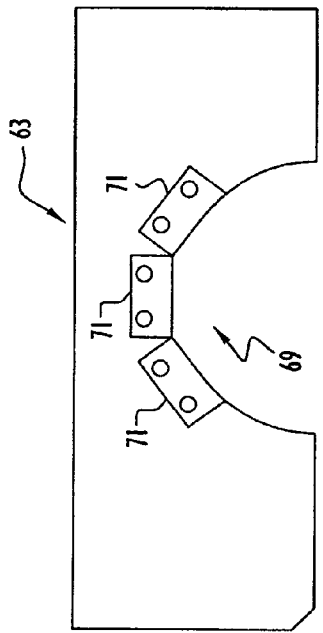
FIG. 18 is a view in elevation of a portion of a drip detector of the temperature control system of FIG. 11 having infrared detectors to detect drips of infused liquid.
Figure 17:
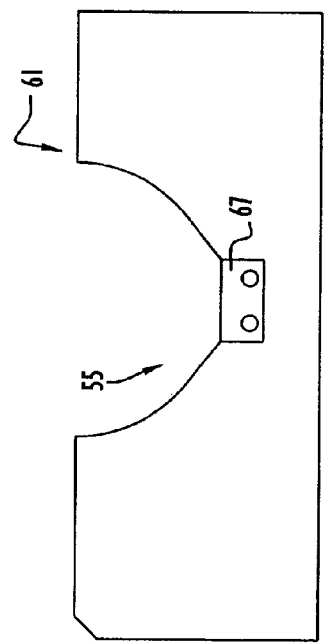
FIG. 17 is a view in elevation of a portion of a drip detector of the temperature control system of FIG. 11 having an infrared emitter to detect drips of infused liquid.

Drip detector 60 utilizes infrared emitters and detectors, typically manufactured by Honeywell, to sense the presence of a drip within the drip chamber as illustrated in FIGS. 17-18. Specifically, drip detector 60 (FIG. 11) includes a substantially rectangular housing having an opening defined through the approximate center of the housing to enable drip chamber 58 to be disposed through the opening. However, the housing may be of any shape or size and may be constructed of any suitable materials. The housing includes a pair of substantially symmetrical housing blocks 61, 63 housing an infrared emitter and infrared detectors, respectively. Housing block 61 is substantially rectangular having a truncated or cut-off upper side corner (e.g., left side upper corner as viewed in FIG. 17) and a substantially semi-circular recess 55 extending from an upper block edge toward the approximate center of the block. An infrared emitter 67 is disposed toward the apex of the recess for emitting infrared energy through the drip chamber. Block 63 is substantially similar to block 61 and includes a truncated or cut-off lower side corner (e.g., left side lower corner as viewed in FIG. 18) and a substantially semi-circular recess 69 extending from a lower block edge toward the approximate center of the block. A plurality of infrared detectors 71, preferably three, are positioned toward the recess apex to detect infrared energy emitted from emitter 67. The detectors detect the infrared energy emitted from emitter 67, while substantially rejecting ambient light. Blocks 61, 63 are connected to form the drip detector housing such that the drip chamber is disposed through the generally circular opening formed by block recesses 55, 69 to enable the emitter and detectors to sense drips within the drip chamber.

Emitter 67 emits a broad signal, typically a 50° conical emission, wherein a drip within the drip chamber focuses the signal on any of infrared detectors 71, each generally having a 50° conical window. The infrared detector windows overlap each other to provide a wide drip view and higher count accuracy. The detectors are connected in parallel to each other within system control circuitry (FIG. 20) to allow more current to flow in the detectors, however, this arrangement slightly degrades detector current to opticouplers associated with drip counting circuitry described below. The reduction in current is alleviated by reducing resistance within the circuit. The detectors typically include a high resistance such that when a drip focuses infrared energy on the detectors, the detectors pass a greater amount of current/voltage to the opticouplers. The passage of varying amounts of current and voltage form a sinusoid wave that the drip counting circuitry may detect and count as pulses. Detectors 71 typically generate analog wave pulses that are counted by the drip counting circuitry during a specified time interval. One pulse typically includes three-hundred sixty degrees of the analog wave. A continuous or free-flow (e.g., no drips, but rather, a continuous stream) of liquid virtually always focuses infrared energy onto a detector, thereby enabling the detectors to pass a relatively high constant amount of current/voltage to the opticouplers. Similarly, an interruption in liquid flow enables the detectors to pass a relatively low constant amount of current/voltage to the opticouplers since the infrared energy is not focused on any detector. Since a continuous or free-flow of liquid and an interruption in liquid flow each pass a relatively constant amount of current/voltage to the opticouplers, the drip counting circuitry does not detect pulses and typically produces a zero count in response to these occurrences.

Alternatively, the detectors may generate a high output and transition to a low output when infrared energy is not detected (i.e., when drips pass through the infrared emission pattern). A high to low transition within the detector output indicates the presence of a drip since the drip prevents the detectors from sensing the infrared energy. A continuous or free-flow of liquid enables the detectors to generate a relatively constant high output, while an interruption in liquid flow enables the detectors to generate a relatively constant low output. Since a continuous or free-flow of liquid and an interruption in liquid flow do not produce any transitions, a zero count is typically produced in response to these occurrences. It is to be understood that the detectors may be implemented to generate low to high transitions in response to detecting a drip wherein the detectors sense drips in substantially the same manner described above. Since the size of a drip varies with tubing size and typically changes shape between the top and bottom of a drip tube (e.g., forming the drip chamber), the detectors are typically positioned such that their overlapping windows cover all areas of the drip tube to ensure that a drip is not missed. Thus, a drip is detected even if the drip tube is slanted and the drip does not pass through the center of the drip chamber. The detectors are generally spaced by approximately 24.4°, however, the detectors may be spaced by any amount (e.g., 37°) based on the area needed to be covered and the angle of the conical window. Generally, the angular spacing of detectors 71 may be varied by approximately five degrees (e.g., plus or minus five degrees) for the arrangement described above. Any quantity of emitters and detectors having dispersion and detection patterns of various angles with the emitters having the same or different angles as the detectors may be utilized, depending upon the strength of signals and areas covered. The emitters and detectors may be positioned in any fashion and may be implemented by any conventional or other types of emitters and detectors that accommodate various forms of energy (e.g., light, specific signal frequencies, etc.)

Figure 19:
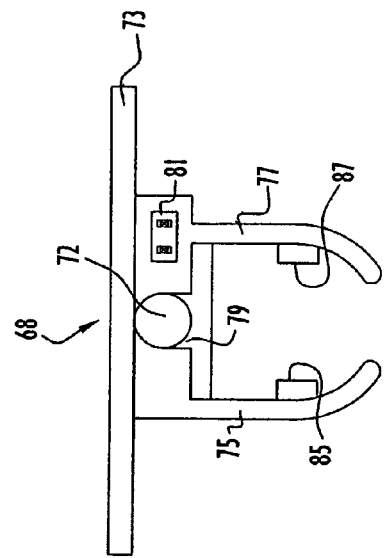
FIG. 19 is a view in elevation of a thermocouple holder of the temperature control system of FIG. 11 for maintaining a temperature sensor in the proper position to provide an accurate temperature measurement of liquid within an intravenous or other tube.

Referring to FIG. 19, thermocouple holder 68 includes a substantially flat rectangular base or platform 73, having curved prongs 75, 77 extending down from the platform and curving toward each other. Prongs 75, 77 each include transversely extending projections 85, 87 that extend from their respective prongs toward each other. A channel 79 is disposed below platform 73 to receive tube 72 (FIG. 11), while temperature sensor 86 (FIGS. 13-15) is disposed between projections 85, 87 of prongs 75, 77 proximate tube 72 to obtain an accurate temperature measurement of the liquid in the tube. The thermocouple holder is typically attached to a patient with platform 73 interfacing a patient body part, such as an arm. The thermocouple holder ensures proper mounting of temperature sensor 86 and enables accurate temperature control via a precise temperature measurement of liquid within tube 72 (i.e., not skin or ambient temperature) wherein the temperature sensor provides a true liquid temperature measurement. The temperature sensor is typically matched to the safety controller described above to provide accuracy and increased sensitivity and precision. A safety circuit 81 is disposed adjacent channel 79 between platform 73 and prong 77. The safety circuit must be complete or closed to enable operation of the system. The heat controller described above monitors the circuit and disables operation when the circuit is broken or open. The safety circuit may include a resistor across wires that creates a specific resistance detected by the heat controller. Alternatively, the safety circuit may be implemented by a Hall effect transistor that switches based on magnetic fields. Magnetic beads may be disposed within the thermocouple holder wherein the beads are matched to the transistor (e.g., as to strength of the field). The transistor senses the beads to enable system operation. Thermocouple holder 68 and tube 72, typically with Luer locks (e.g., male and female), are generally disposable wherein thermocouple holder 68 is typically attached (e.g., via an approved medical biocompatible adhesive) to a patient near the entry site for infused liquids. The thermocouple holder may be implemented with a butterfly base, may be attached to a patient in any fashion at any location, may be of any size or shape and may be constructed of plastic or any other suitable materials, however, by way of example only, the holder has a height slightly less than approximately one inch and a width (e.g., between prongs) of slightly less than approximately one-half inch.

Figure 20:
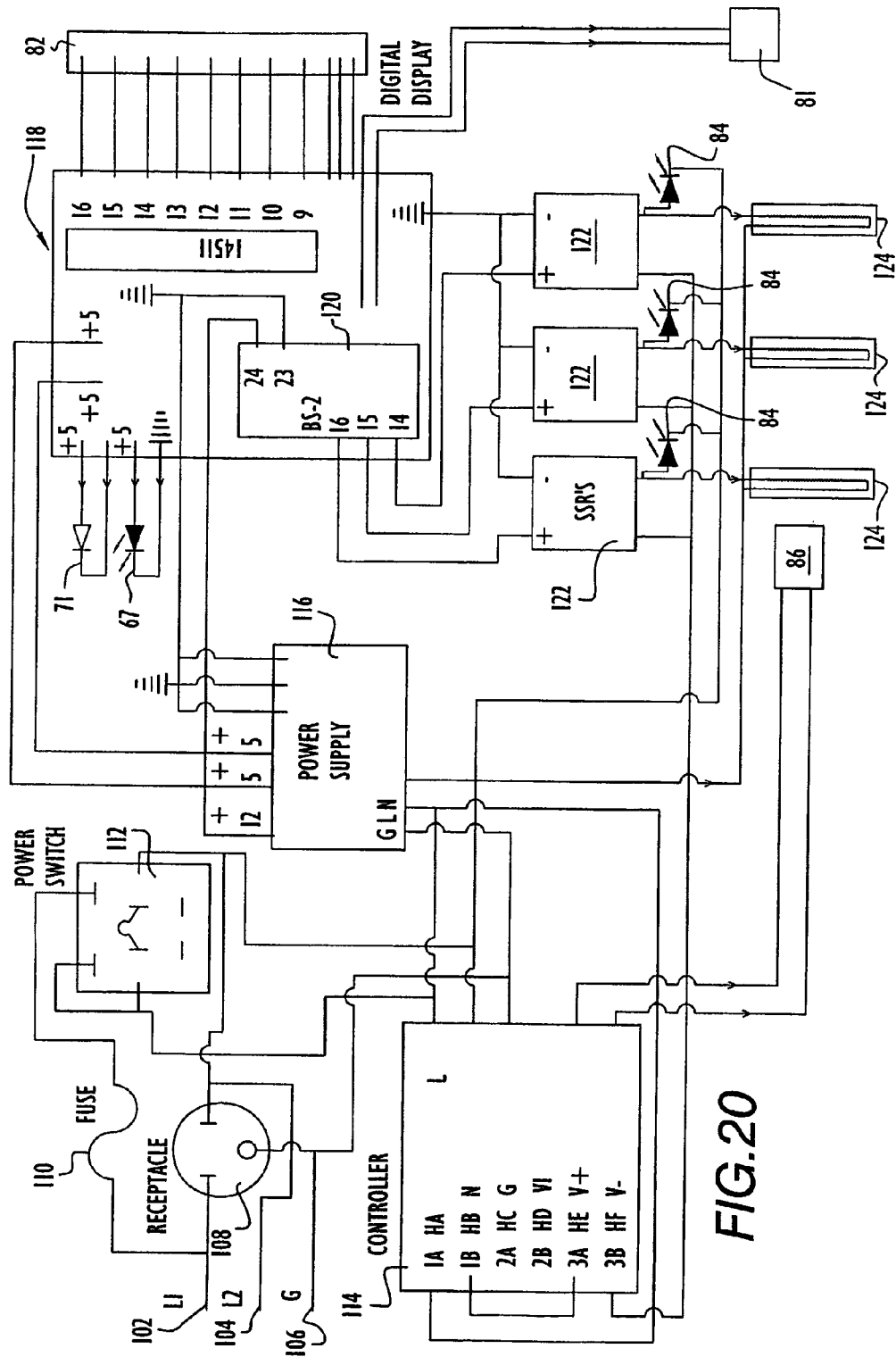
FIG. 20 is an electrical schematic diagram of an exemplary control circuit of the temperature control system of FIG. 11 for controlling system operation.

A circuit for controlling system operation is illustrated in FIG. 20. Specifically, the control circuit includes lines 102, 104 and 106 extending from a common wall outlet jack receptacle 108. A fuse 110 is connected in series with line 102 from receptacle 108 between the receptacle and a power switch 112. Power switch 112 enables power to the circuit from lines 102, 104 (e.g., line voltage (e.g., 120V AC) is typically provided to a power supply 116, the load side of solid state relays 122 and a safety controller 114 each described below). Power supply 116, typically 120V AC having +/-12V DC, +/-5V DC, +5V and -5V DC outputs (e.g., fused at the power supply and generally on the device (e.g., control circuit and/or circuit board 118)), is connected to power switch 112 and provides power to safety controller 114, a circuit board 118, and heaters 124. All control and processor functions are performed at low voltage. Safety controller 114, typically implemented by a Love or Eurotherm controller, receives power from power supply 116 and a temperature signal from temperature sensor 86 (e.g., an RTD sensor is typically utilized with a Love controller, while an infrared sensor is typically utilized with a Eurotherm controller) indicating the temperature of the liquid. Safety controller 114 may alternatively be implemented by any conventional or other processor, controller or circuitry. The true temperature is received by safety controller 114 from the infrared sensor such that no additional calculations are required. The safety controller, typically implemented as a safety override, respectively displays the liquid and set point temperatures on displays 74, 76 (FIG. 12), and is connected in series to a plurality of solid state heat relays 122 that control power to heaters 124, or an alarm relay (not shown). Each solid state relay is further connected to an indicator light 84 of control panel box 70 to indicate the status (i.e., on/off) of a corresponding heater. When the temperature signal from temperature sensor 86 indicates that the liquid temperature equals or exceeds a predetermined or desired liquid temperature, safety controller 114 disables power (e.g., cuts line voltage or opens relays 122) to heaters 124. If temperature sensor 86 fails, safety controller 114 defaults to open circuit (e.g., opens relays 122 to disable heaters 124) and the display flashes alarm. The Eurotherm controller includes a sensor brake alarm loop, temperature response alarm loop and a high temperature alarm, while the Love controller includes a high temperature alarm and sensor brake alarm loop.

Circuit board 118 houses the circuitry that maintains a drip count and controls heaters 124 in response to liquid flow rate. The circuit board includes a heat controller or processor 120 that, via software, manipulates solid state relays 122 to control individual heaters 124 in response to drip counts. The processor, preferably a Parallax BS2 (i.e., Basic Stamp configuration), typically utilizes binary, hexadecimal and Basic programming and includes defaults of no outputs and inputs on (e.g., the processor defaults to having no outputs). Each software instruction is typically executed within one microsecond and the processor includes 5V, 25 ma (i.e., milliamp) outputs for control of the temperature control system. The circuit board further receives signals from safety circuit 81 to disable the system when a complete circuit is not detected, and displays the drip count for a predetermined time interval on display 82. Infrared emitter 67 and detectors 71 are connected to the circuit board wherein detectors 71 transmit signals indicating the presence of a drip as described above to enable the circuit board to count drips. Any quantity of detectors detecting a drip may enable incrementation of the drip count, however, by way of example only, drip detection by any of the detectors increments the drip count. The drip count is sent to processor 120 to manipulate individual heaters as described above.

Figure 21:
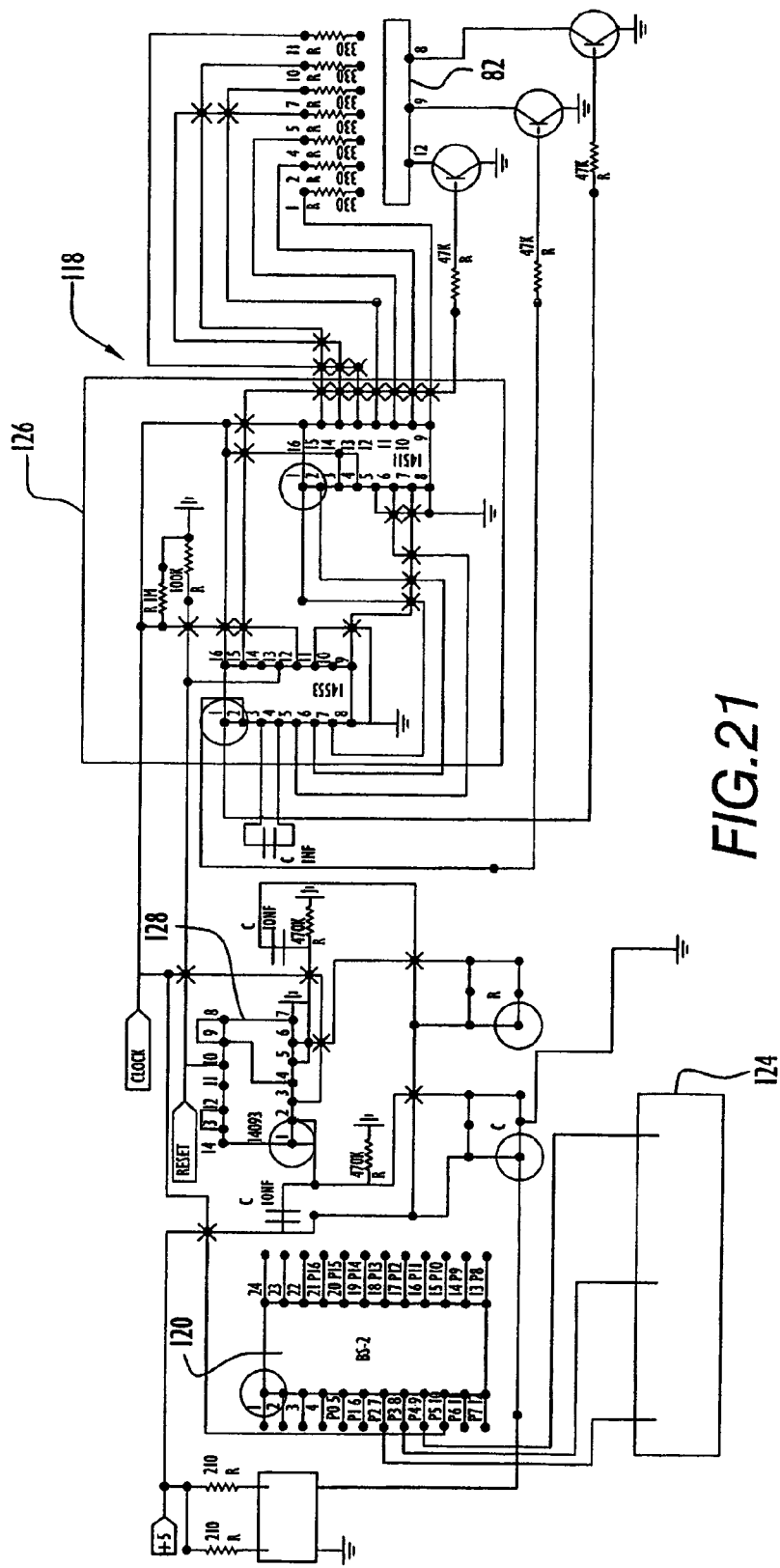
FIG. 21 is an electrical schematic diagram of an exemplary circuit board of the control circuit of FIG. 20.

Referring to FIG. 21, circuit board 118 includes processor 120, opticoupler circuit 128 for infrared emitter and detectors, a counting circuit 126 and display 82. The processor and opticoupler are implemented by conventional integrated circuits, while the counting circuit preferably includes two conventional integrated circuits. The processor, opticoupler and counting circuits may be implemented by any conventional or other circuitry capable of receiving signals from detectors 71 and producing a drip count. Counting circuit 126 increments a count for each drip detected within the drip chamber, and may be reset by processor 120. Infrared detectors 71 are coupled to the counting circuit via opticoupler circuit 128 such that the counting circuit increments the count for each drip detected by the detectors. The opticoupler circuit essentially receives signals from detectors 71 and determines from those signals whether or not a drip is present. The opticoupler subsequently sends a signal to counting circuit 126 to increment the count in response to detection of a drip wherein the count is displayed on display 82. Processor 120 receives the drip count and, in combination with safety controller 114

(FIG. 20), controls heaters 124, via software, to maintain liquid within tube 72 (FIG. 11) at a desired temperature.

Figure 22:
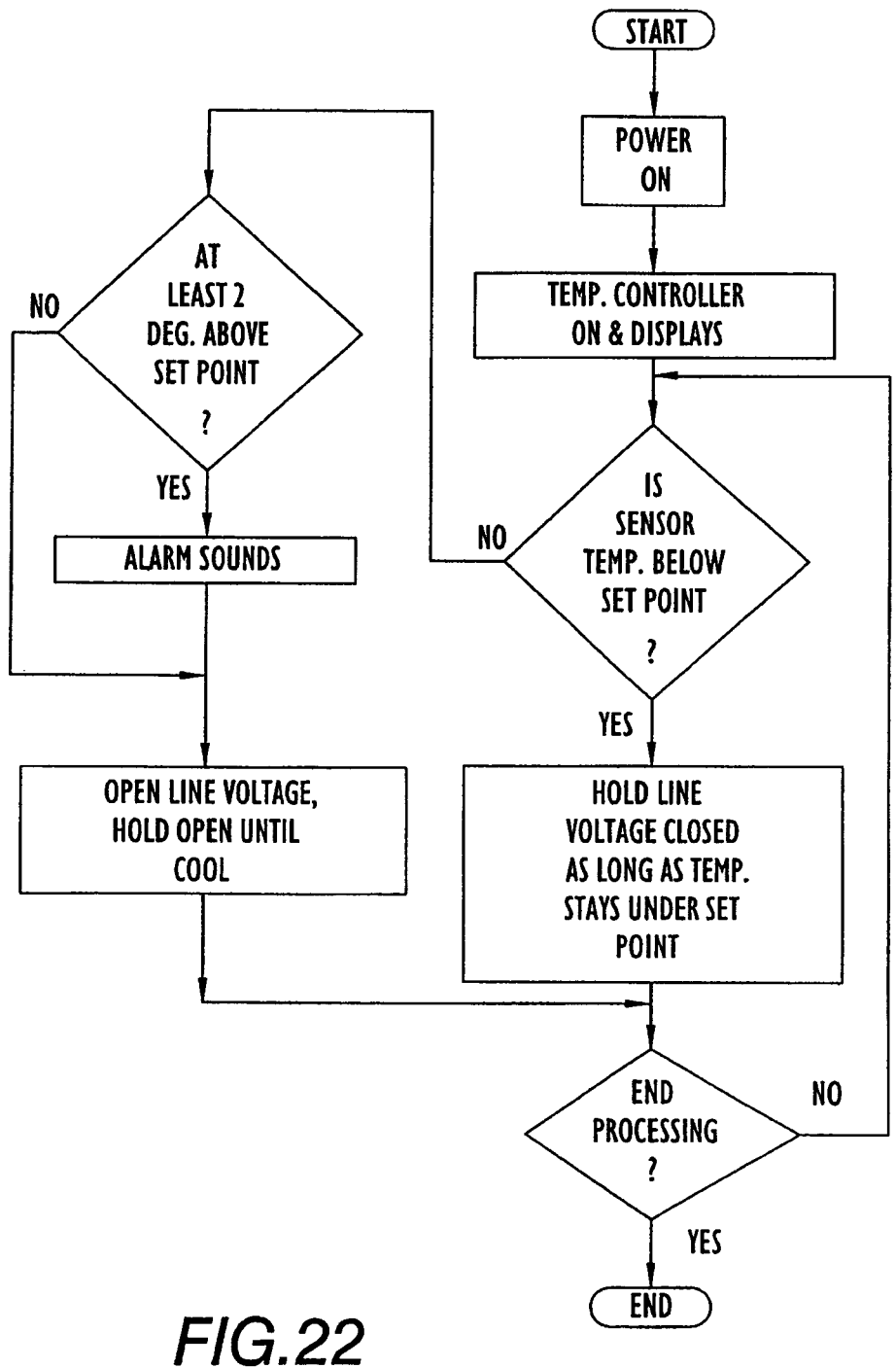
FIG. 22 is a procedural flow chart illustrating the manner in which temperature control system heaters are disabled in response to a liquid temperature measurement being equal to or in excess of a desired liquid temperature within the temperature control system of FIG. 11.

A procedural flow chart for safety controller 114 to display measured liquid and set point temperatures and control heaters 124 in response to liquid temperatures is illustrated in FIG. 22. Specifically, safety controller 114 (FIG. 20) is enabled and displays the liquid temperature detected by temperature sensor 86 and the set point temperature (i.e., predetermined or desired liquid temperature) entered via buttons 78 (FIG. 12) on displays 74, 76, respectively. The sensed temperature is compared to the set point temperature by the safety controller to determine if the sensed temperature is below the set point temperature. The safety controller sounds an alarm when the sensed temperature exceeds the set point temperature by at least two degrees (e.g., Fahrenheit or Celsius depending upon the scale utilized), while disabling power to heaters 124 (e.g., cutting line voltage or opening solid state relays 122) in response to the sensed temperature being equal to or exceeding the set point temperature by any margin. However, the safety controller may be programmed to sound the alarm when the sensed temperature exceeds the set point temperature by any desired amount. If the sensed temperature is below the set point temperature, the safety controller maintains power to heaters 124 (e.g., maintains line voltage or closes solid state relays 122) to enable heat controller or processor 120 to control temperature of the liquid based on measured drip counts as described below. Safety controller 114 repeatedly compares sensed liquid temperatures to the set point temperature to control heaters 124 as described above until processing is complete (e.g., power down of the system). Disablement of heaters 124 by the safety controller overrides any controls issued by the heat controller, however, the heat controller continues to generate heater controls as described below whether or not the heater controls are overridden by the safety controller.

Figure 23:
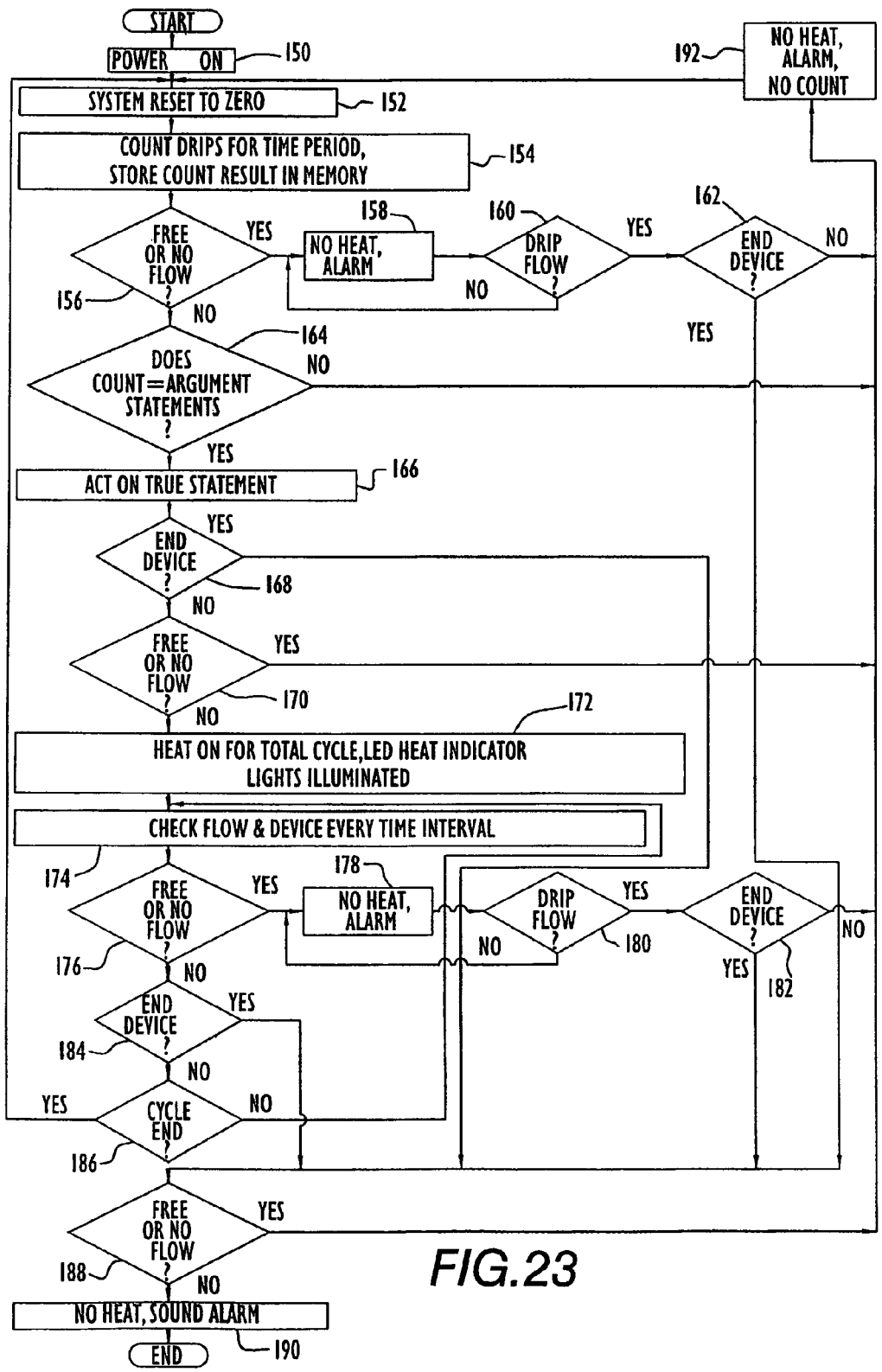
FIG. 23 is a procedural flowchart illustrating the manner in which temperature control system heaters are controlled based on flow rate within the temperature control system of FIG. 11.

A procedural flowchart for heat controller or processor 120 (FIG. 20) to control heaters 124 based on liquid flow rate is illustrated in FIG. 23. The processor software is implemented such that only one command or step may be performed at any one time in sequential order. Generally, processor 120 requests the drip counting circuitry (e.g., the infrared detectors, opticoupler circuit and counting circuit (FIG. 21)) to generate drip counts for predetermined time intervals wherein the processor utilizes the drip counts to control heaters 124. Processor 120 further monitors liquid flow and disables heaters 124 in response to detecting a free-flow of liquid or an interruption of liquid flow to prevent residual heat from reaching a patient. In addition, processor 120 disables system operation in response to safety circuit 81 being open during liquid flow (e.g., the safety circuit is open when a free-flow of liquid or an interruption of liquid flow has each not occurred). Specifically, power is enabled to processor 120 at step 150 and the processor resets the system at step 152 by initializing variables and system parameters to particular values (e.g., zero). The processor requests that a drip count be generated by the drip counting circuitry for a predetermined time interval at step 154 wherein the drip count result is stored in memory, while changes in the drip count are also stored in memory during software execution. The drip count is inspected by the processor at step 156 to determine whether or not a free-flow of liquid or an interruption of liquid flow has occurred (e.g., a drip count of zero for a predetermined time interval indicates a free-flow of liquid or an interruption of liquid flow as described above). If a free-flow of liquid or an interruption of liquid flow has occurred (e.g., the drip count for a predetermined time interval equals zero), processor 120, at step 158, disables heaters 124 and sounds an alarm until the processor determines at step 160 that the liquid flows at a drip flow rate (e.g., until the drip detector senses drips within the drip chamber or, in other words, the drip count for a predetermined time interval is greater than zero).

When the processor determines at step 160 that the liquid flows at a drip flow rate, the processor inspects safety circuit 81 at step 162. This is typically accomplished by examining a circuit variable stored within the processor memory and having a value generated from a poll of the safety circuit wherein the circuit variable value corresponds to the safety circuit status. By way of example only, a circuit variable value equal to or greater than one indicates proper operation or a complete safety circuit, however, the circuit variable may have any values to indicate the safety circuit status. If processor 120 determines that safety circuit 81 is complete at step 162 (e.g., the circuit variable has a value equal to or greater than one), the processor disables heaters 124 and sounds an alarm at step 192, and subsequently resets the system for a new cycle at step 152. Otherwise, in response to determining that the safety circuit is open at step 162 (e.g., the circuit variable has a value less than one), processor 120 inspects the drip count at step 188 to detect a free-flow of liquid or an interruption in liquid flow. When a free-flow of liquid and an interruption of liquid flow has each not occurred (e.g., the drip count for a predetermined time interval is greater than zero), processor 120 disables heaters 124 and sounds an alarm at step 190, and subsequently terminates system operation. However, in response to detecting a free-flow of liquid or an interruption of liquid flow at step 188 (e.g., the drip count for a predetermined time interval equals zero), processor 120 disables heaters 124 and sounds an alarm at step 192, and subsequently resets the system for a new cycle at step 152.

In response to determining at step 156 that a free-flow of liquid and an interruption of liquid flow has each not occurred (e.g., the drip count for a predetermined time interval is greater than zero), processor 120 utilizes the drip count to determine, at step 164, an appropriate control scheme for heaters 124 (e.g., the specific heaters to activate and the length of time of their activation). Specifically, the drip count is compared to values within a series of logical expressions formed in a priority hierarchy with instructions (e.g., heater control schemes) associated with higher priority expressions executed first. The instructions associated with a first true logical expression are executed even if other lower expressions are true. If the drip count does not correspond with a heater control scheme (e.g., the drip count does not correspond to a particular count or range associated with a control scheme), processor 120 disables heaters 124 and sounds an alarm at step 192, and subsequently resets the system for a new cycle at step 152. When a drip count corresponds to a heater control scheme (e.g., the drip count corresponds to a particular count or range associated with a control scheme), that heater control scheme is executed at step 166.

Processor 120, at initial execution of a control scheme, inspects safety circuit 81 at step 168. If processor 120 determines at step 168 that safety circuit 81 is not complete (e.g., the circuit variable has a value less than one), the processor inspects the drip count at step 188 to detect a free-flow of liquid or an interruption of liquid flow. When a free-flow of liquid and an interruption of liquid flow has each not occurred (e.g., the drip count for a predetermined time interval is greater than zero), processor 120 disables heaters 124 and sounds an alarm at step 190, and subsequently terminates system operation. However, in response to detecting a free-flow of liquid or an interruption of liquid flow at step 188 (e.g., the drip count for a predetermined time interval equals zero), processor 120 disables heaters 124 and sounds an alarm at step 192, and subsequently resets the system for a new cycle at step 152. When processor 120 determines at step 168 that safety circuit 81 is complete (e.g., the circuit variable has a value equal to or greater than one), the processor determines at step 170 whether or not a free-flow of liquid or an interruption of liquid flow has occurred. If a free-flow of liquid or an interruption of liquid flow has occurred (e.g., the drip count for a predetermined time interval equals zero), processor 120 disables heaters 124 and sounds an alarm at step 192, and subsequently resets the system for a new cycle at step 152.

When processor 120 respectively determines at steps 168 and 170 that safety circuit 81 is complete (e.g., the circuit variable has a value equal to or greater than one) and a free-flow of liquid and an interruption of liquid flow has each not occurred (e.g., the drip count for a predetermined time interval is greater than zero), processor 120 performs the control scheme associated with the drip count at step 172 wherein specific heaters 124 are activated for a particular time interval, while the appropriate heater indicator lights are illuminated. During a heating cycle, processor 120, at step 174, conducts an inspection approximately every ten seconds or any other time interval to ensure that safety circuit 81 remains complete and that the liquid flow has not been changed (e.g., user intervention to enable free-flow of liquid or an interruption of liquid flow). If processor 120 determines at step 176 that liquid flow has been altered (e.g., the drip count for a predetermined time interval equals zero indicating a free-flow of liquid or an interruption of liquid flow), processor 120, at step 178, disables heaters 124 and sounds an alarm until the processor determines at step 180 that the liquid flows at a drip flow rate (e.g., the drip count for a predetermined time interval is greater than zero) as described above.

When processor 120 determines at step 180 that the liquid flows at a drip flow rate, the processor inspects safety circuit 81 at step 182. If processor 120 determines that safety circuit 81 is complete at step 182 (e.g., the circuit variable has a value equal to or greater than one), the processor disables heaters 124 and sounds an alarm at step 192, and subsequently resets the system for a new cycle at step 152. Otherwise, in response to determining that safety circuit 81 is open at step 182 (e.g., the circuit variable has a value less than one), processor 120 inspects the drip count at step 188 to detect a free-flow of liquid or an interruption in liquid flow. When a free-flow of liquid and an interruption of liquid flow has each not occurred (e.g., the drip count for a predetermined time interval is greater than zero), processor 120 disables heaters 124 and sounds an alarm at step 190, and subsequently terminates system operation. However, in response to detecting a free-flow of liquid or an interruption of liquid flow at step 188 (e.g., the drip count for a predetermined time interval equals zero), processor 120 disables heaters 124 and sounds an alarm at step 192, and subsequently resets the system for a new cycle at step 152.

Referring back to step 176, when a free-flow of liquid and an interruption of liquid flow has each not occurred (e.g., the drip count for a predetermined time interval is greater than zero), processor 120 inspects safety circuit 81 at step 184. If processor 120 determines at step 184 that safety circuit 81 is not complete (e.g., the circuit variable has a value less than one), the processor inspects the drip count at step 188 to detect a free-flow of liquid or an interruption of liquid flow. When a free-flow of liquid and an interruption of liquid flow has each not occurred (e.g., the drip count for a predetermined time interval is greater than zero), processor 120 disables heaters 124 and sounds an alarm at step 190, and subsequently terminates system operation. However, in response to detecting a free-flow of liquid or an interruption of liquid flow at step 188 (e.g., the drip count for a predetermined time interval equals zero), processor 120 disables heaters 124 and sounds an alarm at step 192, and subsequently resets the system for a new cycle at step 152.

When processor 120 respectively determines at steps 176 and 184 that a free-flow of liquid and an interruption of liquid flow has each not occurred (e.g., the drip count for a predetermined time interval is greater than zero) and that safety circuit 81 is complete (e.g., the circuit variable has a value equal to or greater than one), the processor determines at step 186 whether or not a control scheme or cycle is complete. In response to completion of a cycle, processor 120 resets the system for a new cycle at step 152; otherwise, the processor continues inspecting liquid flow and the safety circuit at predetermined time intervals as described above (i.e., steps 174, 176, and 184) until the cycle is complete. Heaters 124 are controlled by processor 120 in the manner described above wherein the heaters function in accordance with controls received from processor 120 unless safety controller 114 disables the heaters as described above. However, processor 120 continues to generate controls for heaters 124 as described above whether or not the controls from the processor have been overridden by the safety controller. In other words, processor 120 continues to generate heater controls even if the heaters are prevented from functioning in response to those controls.

The temperature control system may further include multiple chips (e.g., controllers) to permit greater simultaneous functionality (e.g., temperature control of multiple bags having different uses, such as intravenous and irrigation). Further, the temperature control system may be controlled via a personal or other type of computer from a remote location, such as a lab. The remote system may control temperature and flow rate wherein troubleshooting may further be accomplished via modem from a remote location.

Figure 24:
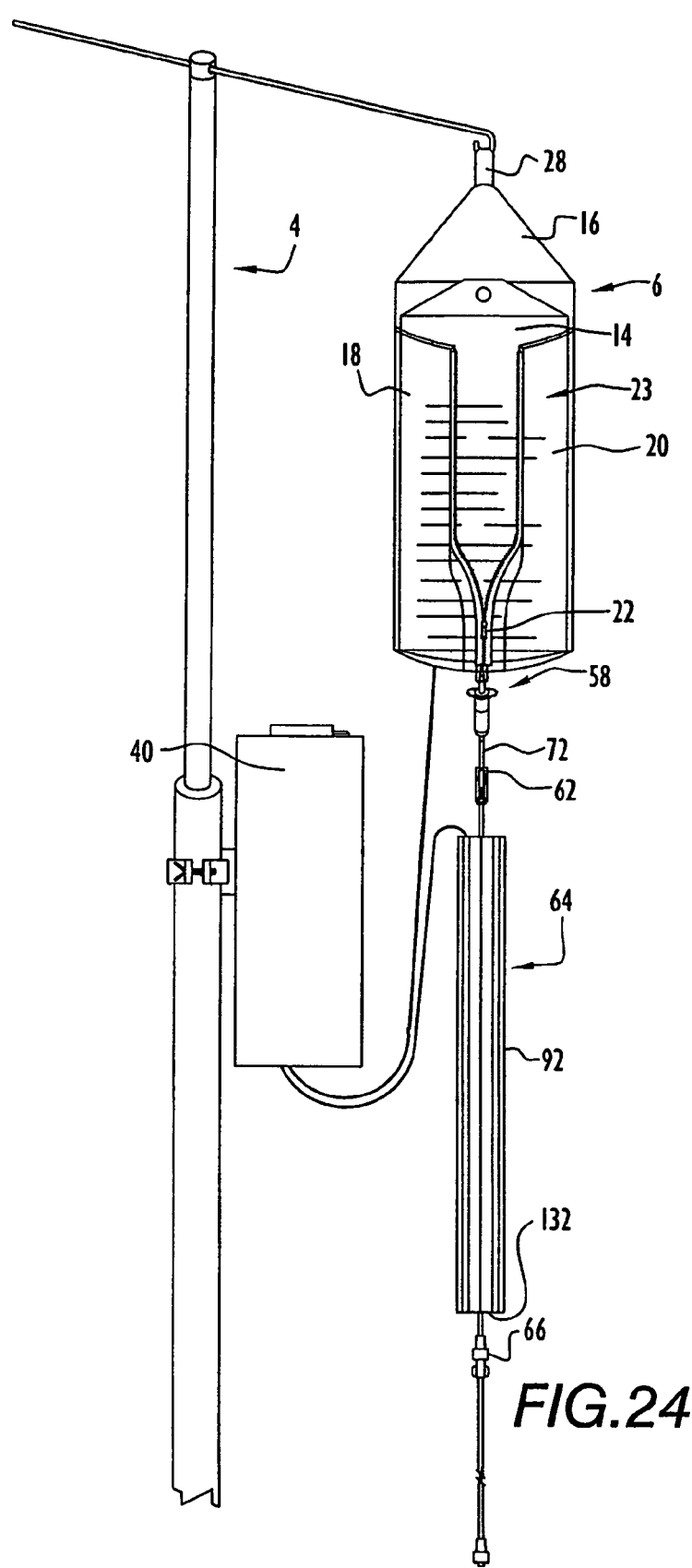
FIG. 24 is a view in perspective of a temperature control system for infused liquids heating both a liquid-filled bag and liquid within an intravenous or other tube according to still another embodiment of the present invention.

Alternatively, heating assembly 64 may contain a single heater and be used in combination with a heated liquid-filled bag as illustrated in FIG. 24. Specifically, the configuration illustrated in FIG. 24 is similar to the configuration illustrated in FIG. 11 and includes receptacle 6, drip chamber 58, tube 72, roller lock 62 and connector 66, each as described above for FIG. 11. The configuration further includes control box 40, as described above for FIG. 11, housing a heater control circuit (FIG. 25) and a heating assembly 64 that is substantially similar to the heating assembly described above for FIGS. 13-15 except that a single elongated heater or heating element 132 is utilized within heating assembly sleeve 92. Heater 132 is similar to heating element 36 (FIG. 9) described above, and is controlled by a controller based on sensed resistance in heater 132 in substantially the same manner described above for the heated pressurized infusion system. Receptacle 6 typically contains liquid-filled bag 14, conductive plate 38 (FIG. 8) and heating element 36 (FIG. 9) as described above for the heated pressurized infusion system. The heating element and conductive plate may be disposed on a bellows bag 32 (FIG. 5), containing a bellows and positioned adjacent the liquid-filled bag within receptacle 6, to heat the liquid-filled bag as described above. However, the heating element and conductive plate may be utilized without the bellows and bellows bag and may be disposed within the receptacle in any fashion. Drip chamber 58 is coupled to liquid-filled bag 14 wherein tube 72 extends from the drip chamber and traverses roller lock 62, heating assembly 64 and connector 66 as described above for FIG. 11 to direct heated liquid from the liquid-filled bag to an entry site on a patient. A portion of tube 72 is disposed within heating assembly sleeve 92 as described above to enable heating assembly 64 to maintain the heated liquid at a desired temperature and prevent liquid cooling as the heated liquid flows within the tube from liquid-filled bag 14 to a patient.

Figure 25:
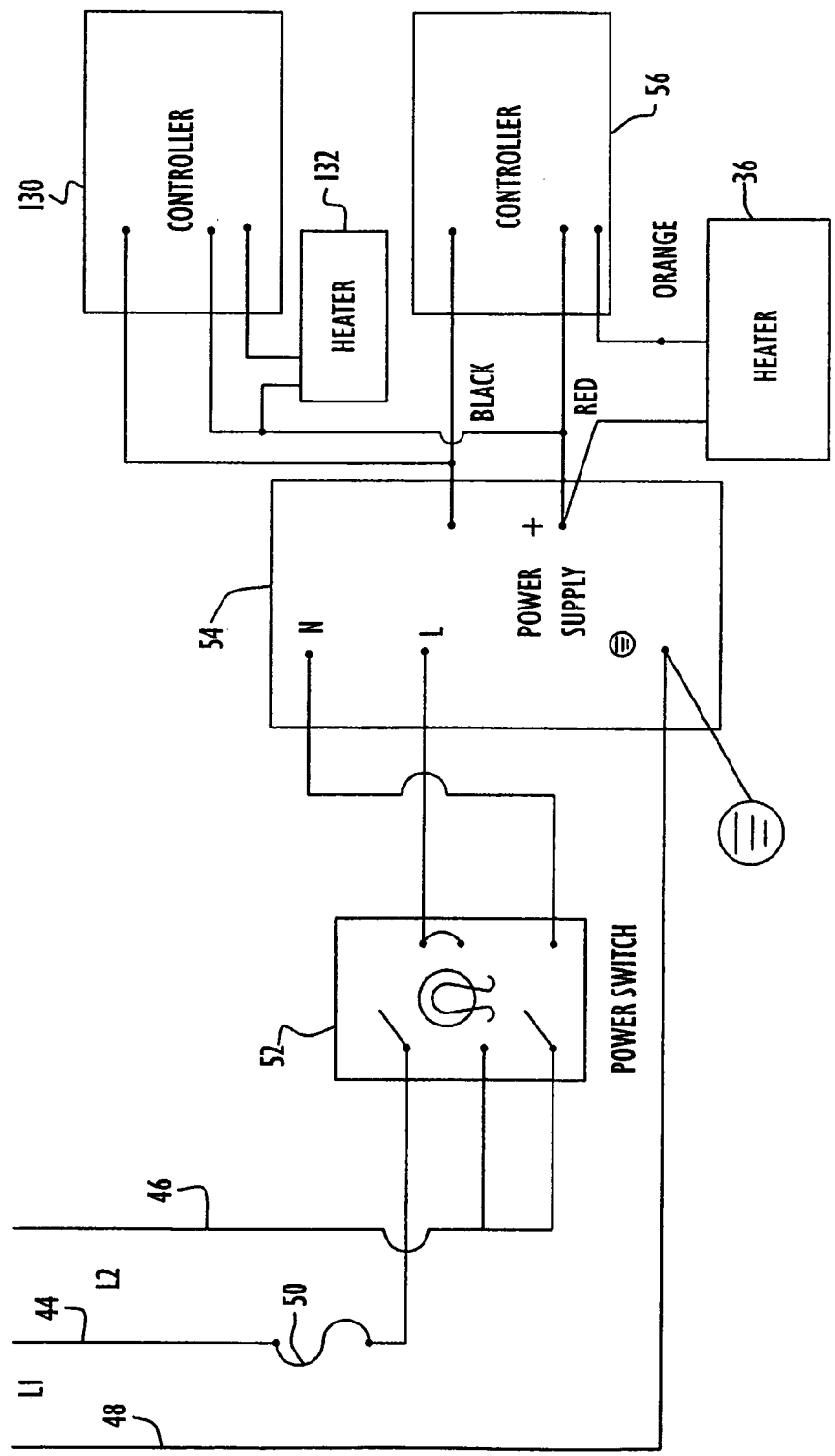
FIG. 25 is an electrical schematic diagram of an exemplary control circuit for the temperature control system of FIG. 24.

A control circuit for controlling heating element 36 and heater 132 is illustrated in FIG. 25. The control circuit is substantially similar to the circuit described above for FIG. 10 except that the control circuit includes an additional controller 130 to control heater 132 of heating assembly 64. Controller 130 is substantially similar to controller 56 and controls power to heater 132. Specifically, power switch 52 enables power to power supply 54 as described above wherein the power supply directs power to controllers 56, 130 and corresponding heating element 36 and heater 132, respectively. Controller 56 senses resistance within heating element 36 and controls power to the heating element to maintain the heating element and liquid-filled bag at a desired temperature as described above. Controller 130 senses resistance within heater 132 and controls power to that heater in substantially the same manner described above for controller 56 to maintain the heater and heated liquid within tube 72 at a desired temperature as the heated liquid flows within the tube from the liquid-filled bag to a patient.

It will be appreciated that the embodiments described above and illustrated in the drawings represent only a few of the many ways of implementing a method and apparatus for pressure infusion and temperature control of infused liquids.

The various embodiments of the present invention, namely the pressurized infusion systems and the temperature control systems may be utilized either individually or in any combination to warm liquid. For example, the non-heated pressurized infusion system may be utilized individually or in combination with the multiple heater temperature control system, while the heated pressure infusion system may be utilized individually or in combination with the single heater temperature control system. Further, the systems may be utilized for any applications requiring heated fluids, or fluids heated during fluid flow.

The receptacle may be of any shape or size, and may be constructed of any suitable materials. Further, the receptacle may be attached to intravenous poles or other structures via any type of hook, opening or by any other fastening techniques. The receptacle may include any type of zipper or other fastening devices disposed anywhere on the receptacle in any fashion to close the compartment. The pressure gauge may be implemented by any conventional or other type of device for measuring and indicating pressure levels, and may be disposed on the receptacle, intravenous pole or at any other location capable of conveying pressure readings to a user.

The bellows may be implemented by any inflatable device capable of expanding upon inflation, and may be inflated via any type of fluid, such as a gas (e.g., air) or liquid. The bellows may be of any shape or size capable of applying pressure to the liquid-filled bag, may be constructed of any suitable materials, and may be oriented in any fashion within the bellows bag or receptacle. Further, any quantity (e.g., at least one) of bellows may be utilized to apply pressure to the liquid-filled bag in substantially the same manner described above. The bellows port may be disposed anywhere on the bellows. The bellows may be utilized without being disposed within the bellows bag. The bellows bag may be of any shape or size capable of receiving the bellows or covering any portion of the bellows, and may be constructed of any suitable materials. The bellows bag opening may be of any shape or size and may be disposed anywhere on the bellows bag capable of enabling insertion of the bellows into the bellows bag. The bellows bag opening may be covered by any flap or other object to maintain the bellows within the bellows bag. The port opening in the bellows bag may be of any shape or size and may be disposed at any location capable of enabling fluid transfer between the bellows and an inflation/deflation device. The hose for directing fluid to and from the bellows may be implemented by any conventional or other type of hose or tube, may be of any size or shape, and may be constructed of any suitable materials. The bellows bag opening may alternatively be utilized for receiving hoses or tubes for facilitating fluid transfer between the bellows and an inflation/deflation device. The bellows bag pocket may be of any shape or size, and may be disposed anywhere on the bag to enable the heating element and conductive plate to be applied to the liquid-filled bag. The bellows may be inflated by any type of inflating device or pump including any type of valve or other device for controlling inflation and deflation of the bellows.

The heating element and conductive plate may be of any shape or size, and may be constructed of any materials capable of conducting heat. The heating element may be utilized without the conductive plate, may be disposed adjacent the liquid-filled bag, and may be implemented by any type of heater or heating element. The heating element and conductive plate may alternatively be disposed anywhere proximate the liquid-filled bag to heat that bag, and not necessarily within the receptacle. The pressurized and heated pressurized infusion systems are not limited to application with intravenous poles, but may be utilized with various structures.

The heating element temperature may be measured by any conventional or other type of temperature measuring devices to control heating element temperature. The heating element control circuitry may include any conventional or other type of power switch (e.g., lighted), power supply and controller. The heating element controller is typically implemented by a commercially available controller pre-programmed and loaded with its own software, but may be implemented by any conventional or other type of controller, microprocessor, or circuitry capable of controlling the heating element to attain a desired temperature. The control box may be of any shape or size, and may be constructed of any suitable materials. The control box may be disposed on an intravenous pole or at any location capable of enabling the heating element control circuit to control the heating element.

The control panel box may be of any shape or size, and may disposed anywhere on an intravenous pole or at any other location capable of controlling the heating assembly. The control panel front surface may include any types of displays, lights or other indicators, or switches (e.g., lighted) arranged in any fashion. The displays may be implemented by any conventional or other types of displays, such as LED or LCD displays. The indicator lights may be implemented by any type of light or other indicator, such as audio, voice or display, to indicate heater activation. The power switch may be implemented by any type of conventional or other type of switch or button that may include a light for illuminating the switch or button. The displays may display any quantity of digits to reflect the actual and set point temperatures.

The heating assembly sleeve may be of any shape or size, and may be constructed of any suitable materials. The slot may be of any length and be defined anywhere in the sleeve to engage the tube. Alternatively, the sleeve may include any type of fastener to engage the tube. The sleeve may include channels or other openings disposed anywhere on the sleeve to accommodate wiring. The heaters may be disposed anywhere within or adjacent the sleeve capable of heating the tube. The sleeve may include any quantity of heaters (e.g., at least one) to heat the tube. The sleeve may be encased by a jacket of any shape or size and constructed of any suitable materials. The jacket may include any type of zipper or other fastener to maintain the sleeve within the jacket. The temperature sensor may be implemented by any conventional or other type of infrared, resistive temperature (RTD) or other temperature sensing devices. The heating assembly may be disposed anywhere along the tube and accommodate any sized portion of the tube to heat the liquid, while the tube may be implemented by any conventional intravenous or other type of tube. The drip chamber may be implemented by any conventional drip chamber or other device that enables the fluid to drip. The drip detector may include any type of mechanical or other type of detector to detect drips. The emitter may be implemented by any conventional infrared or other type of emitter to detect the drip, such as emitters for transmitting signals at infrared or any other frequency or light band. The detectors may be implemented by any conventional infrared or other type of detector capable of detecting the signal emitted by the emitter. The drip detector may include any quantity of emitters and detectors (e.g., at least one emitter and one detector). The drip detector housing may be of any shape, and may be constructed of any suitable materials. The drip detector may be disposed at any location near the drip chamber capable of detecting a drip. The emitter may have any type of emission spread (e.g., conical) with any angle, while each detector may include any detection window (e.g., having any angle) to detect the emitter signal. The emitter and detectors may be arranged in any fashion within the drip detector housing to detect a drip.

The control circuitry for the temperature control system may include any conventional or other types of fuses, receptacles, controllers, switches (e.g., lighted), power supplies, and relays. The safety controller is typically implemented by a commercially available pre-programmed controller loaded with its own software, but may be implemented by any type of controller, microprocessor or other circuitry capable of disabling the heaters in response to a temperature measurement. The power supply may be implemented by any conventional or other type of power supply, while the solid state relays may be implemented by any type of solid state or other relays or switches. The power switch may be implemented by any conventional or other type of switch (e.g., lighted) or button. The heat controller may be implemented by any type of controller, microprocessor or other circuitry capable of controlling the heaters in response to flow rate. The heat controller or processor and safety and heating element controllers, if the safety and heating element controllers are implemented by a programmable controller requiring software, may be programmed in any suitable computer language wherein the program and algorithm may be modified in any fashion to control heaters for maintaining liquid temperature. For example, the time intervals for maintaining heater activation may be adjusted to control heating of the liquid within the tube based on a desired drip or flow rate. It is to be understood that one of ordinary skill in the computer and/or programming arts can develop the software for the heat controller or processor and heating element and safety controllers, if the heating element and safety controllers are implemented by programmable controllers requiring software, based on the functional description of controller operation in the specification and flow charts illustrated in the drawings.

The circuit board may include any type of circuitry to interpret detector signals and increment a counter. The counter may be implemented by any conventional or other type of counting circuitry, such as integrated circuits, a microprocessor, registers, memory, etc. The opticouplers may be implemented by any conventional or other type of opticoupler or other circuitry capable of receiving detector signals and determining whether or not to increment a counter.

The thermocouple holder may be of any size or shape, and may be constructed of any suitable materials. The thermocouple holder may receive the tube and sensor in any fashion to enable the sensor to obtain temperature measurement of the liquid within the tube. The holder may be disposed at any location near the entry site, and may be attached to a patient via any suitable fastening technique. The safety circuit may be implemented by any type of circuit enabling operation of the system wherein any values may be utilized within the heat controller to indicate safety circuit status (e.g., complete or open).

The single heater temperature control system may include any type of heating element or heater disposed within the heating assembly. The heating element may be of any size or shape, and may be disposed at any location within the sleeve capable of heating the liquid within the tube. The control circuit of the single heater temperature control system may include any conventional or other type of fuse, power switch (e.g., lighted) or controllers as described above for the control circuit of the heated pressurized infusion system. The controllers of the single heater temperature control system may be implemented by any controllers, microprocessors or other circuitry capable of controlling the heating element and heater in response to a temperature measurement as described above.

It is to be understood that the heating assembly heaters may be controlled by the heat controller based on the relationship between flow rate, liquid viscosity and temperature. The relationship between the viscosity and temperature of any liquid is known. Since the viscosity of the infused liquid is known, and the flow rate is measured, the temperature of the liquid, and hence, heater operation may be controlled based on the known viscosity and measured flow rate. That is, the heat controller may control the heating assembly heaters based on flow rate (e.g., and known viscosity) to maintain liquid temperature at substantially a desired temperature. From the foregoing description, it will be appreciated that the invention makes available a novel method and apparatus for pressure infusion and temperature control of infused liquids wherein an inflatable device is disposed adjacent a liquid-filled bag to apply pressure to the liquid-filled bag to drive liquid from the liquid-filled bag to a patient, while the inflatable device may further include a conductive plate and heating element to apply heat to the liquid-filled bag. Further, a heating assembly including at least one heater may be disposed along an intravenous or other tube to heat liquid flowing within the tube from a liquid-filled bag to a patient.

Having described preferred embodiments of a new and improved method and apparatus for pressure infusion and temperature control of infused liquids, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In an apparatus for controlling temperature of infused liquids as liquid flows from a liquid-filled container through a drip chamber and tube to an entry site on a patient, wherein said drip chamber includes a transparent tube portion and is disposed along said tube subsequent said liquid-filled container, an apparatus for detecting drips within said drip chamber comprising:
  a housing including:
    an opening for receiving said drip chamber;
    a first housing member including an emitter disposed therein for emitting signals through said transparent tube portion in the form of non-visible light to minimize the effect of ambient visible light in the vicinity of said transparent tube portion; and a second housing member coupled to said first housing member to form said opening and including a plurality of detectors disposed therein each for detecting said non-visible light signals emitted by said emitter of said first housing member and modified by drips within said transparent tube portion to sense the presence of drips within said drip chamber, wherein each said detector includes an angular detection window providing view of an area within said transparent tube portion and detects said non-visible light signals within said view, and wherein said plurality of detectors are angularly displaced from each other about said transparent tube and are arranged to include overlapping detection windows for detecting said non-visible light signals emitted through said transparent tube portion by said emitter of said first housing member, wherein at least one angular detection window comprises a conical window.

2. The apparatus of claim 1 wherein said housing includes an exterior surface disposed along a periphery of said opening, and said detectors are disposed within said housing at said exterior surface.

3. The apparatus of claim 2 wherein said emitter is disposed at said exterior surface of said housing.

4. The apparatus of claim 1 wherein said detectors are positioned within said housing to receive said ambient visible light through said transparent tube portion without permitting said received ambient visible light to affect said drip detection.

5. The apparatus of claim 1, wherein:
the emitter generates a broad signal; and
the broad signal is detectable by multiple detectors of the plurality of detectors.

6. The apparatus of claim 1, wherein the emitter generates a broad signal toward multiple detectors of the plurality of detectors.

7. In an apparatus for controlling temperature of infused liquids as liquid flows from a liquid-filled container through a drip chamber and tube to an entry site on a patient, wherein said drip chamber includes a transparent tube portion and is disposed along said tube subsequent said liquid-filled container, an apparatus for detecting drips within said drip chamber comprising:
a housing including:
an opening for receiving said drip chamber;
a first housing member including an emitter disposed therein for emitting signals through said transparent tube portion in the form of non-visible light to minimize the effect of ambient visible light in the vicinity of said transparent tube portion; and
a second housing member coupled to said first housing member to form said opening and including a plurality of detectors disposed therein each for detecting said non-visible light signals emitted by said emitter of said first housing member and modified by drips within said transparent tube portion to sense the presence of drips within said drip chamber, wherein each said detector includes an angular detection window providing view of an area within said transparent tube portion and detects said non-visible light signals within said view, and wherein said plurality of detectors are angularly displaced from each other about said transparent tube and are arranged to include overlapping detection windows for detecting said non-visible light signals emitted through said transparent tube portion by said emitter of said first housing member, wherein the emitter generates a conical signal.

8. The apparatus of claim 7, wherein the signal is a 50° conical signal.

9. In an apparatus for controlling temperature of infused liquids as liquid flows from a liquid-filled container through a drip chamber and tube to an entry site on a patient, wherein said drip chamber includes a transparent tube portion and is disposed along said tube subsequent said liquid-filled container, and said apparatus includes a drip detector having a housing including an opening, a method for detecting drips within said drip chamber comprising:
(a) receiving said drip chamber through said opening of said housing, wherein said housing includes first and second housing members coupled together to form said opening;
(b) emitting signals through said transparent tube portion in the form of non-visible light, via an emitter disposed within said first housing member, to minimize the effect of ambient visible light in the vicinity of said transparent tube portion; and
(c) detecting said non-visible light signals emitted by said emitter of said first housing member and modified by drips within said transparent tube portion, via a plurality of detectors disposed within said second housing member, to sense the presence of drips within said drip chamber, wherein each said detector includes an angular detection window providing view of an area within said transparent tube portion and detects said non-visible light signals within said view, and wherein said plurality of detectors are angularly displaced from each other about said transparent tube and arranged to include overlapping detection windows for detecting said non-visible light signals emitted through said transparent tube portion by said emitter of said first housing member, wherein at least one angular detection window comprises a conical window.

10. The method of claim 9 wherein:
said housing includes an exterior surface disposed along a periphery of said opening, and
step (c) further includes: (c.1) positioning said detectors within said housing at said exterior surface.

11. The method of claim 10 wherein step (c) further includes: (c.2) disposing said emitter at said exterior surface of said housing.

12. The method of claim 9 wherein step (c) further includes: (c.1) positioning said detectors within said housing to receive said ambient visible light through said transparent tube portion without permitting said received ambient visible light to affect said drip detection.

13. The method of claim 9, wherein (b) further comprises (b.1) emitting a broad signal detectable by multiple detectors.

14. The method of claim 9, wherein (b) further comprises (b.1.) emitting a signal toward multiple detectors of the plurality of detectors.

15. In an apparatus for controlling temperature of infused liquids as liquid flows from a liquid-filled container through a drip chamber and tube to an entry site on a patient, wherein said drip chamber includes a transparent tube portion and is disposed along said tube subsequent said liquid-filled container, and said apparatus includes a drip detector having a housing including an opening, a method for detecting drips within said drip chamber comprising:
(a) receiving said drip chamber through said opening of said housing, wherein said housing includes first and second housing members coupled together to form said opening;
(b) emitting signals through said transparent tube portion in the form of non-visible light, via an emitter disposed within said first housing member, to minimize the effect of ambient visible light in the vicinity of said transparent tube portion; and (c) detecting said non-visible light signals emitted by said emitter of said first housing member and modified by drips within said transparent tube portion, via a plurality of detectors disposed within said second housing member, to sense the presence of drips within said drip chamber, wherein each said detector includes an angular detection window providing view of an area within said transparent tube portion and detects said non-visible light signals within said view, and wherein said plurality of detectors are angularly displaced from each other about said transparent tube and arranged to include overlapping detection windows for detecting said non-visible light signals emitted through said transparent tube portion by said emitter of said first housing member, wherein: the signal is conical; and (b) comprises (b.1) emitting a conical signal toward the plurality of detectors.

16. The method of claim 15, wherein the signal is a 50° conical signal.

* * * * *